(12) United States Patent
Caligiuri et al.

(10) Patent No.: US 8,951,743 B2
(45) Date of Patent: Feb. 10, 2015

(54) DETECTION OF SHED CD31, DIAGNOSIS OF ATHEROTHROMBOSIS AND AUTOIMMUNE DISORDERS, AND METHODS FOR ANALYZING SIGNALING PATHWAYS

(75) Inventors: Giuseppina Caligiuri, Paris (FR); Antonino Nicoletti, Paris (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 678 days.

(21) Appl. No.: 13/001,815

(22) PCT Filed: Jun. 30, 2009

(86) PCT No.: PCT/EP2009/058220
§ 371 (c)(1),
(2), (4) Date: Mar. 11, 2011

(87) PCT Pub. No.: WO2010/000756
PCT Pub. Date: Jan. 7, 2010

(65) Prior Publication Data
US 2011/0229981 A1    Sep. 22, 2011

(30) Foreign Application Priority Data

Jun. 30, 2008   (EP) .................................... 08305361
Feb. 9, 2009    (EP) .................................... 09305116

(51) Int. Cl.
*G01N 33/53* (2006.01)
*G01N 33/543* (2006.01)
*G01N 33/68* (2006.01)

(52) U.S. Cl.
CPC ...... *G01N 33/54313* (2013.01); *G01N 33/6878* (2013.01); *G01N 2333/70503* (2013.01); *Y10S 435/968* (2013.01); *Y10S 435/973* (2013.01)
USPC ........ 435/7.2; 435/7.94; 435/173.4; 435/968; 435/973; 436/506; 436/518; 436/523; 436/548; 436/63; 436/171; 436/172

(58) Field of Classification Search
USPC ............ 435/5, 6, 7.1, 7.2, 7.94, 173.4, 287.2, 435/968, 973, 974; 436/501, 507, 518, 523, 436/548, 56, 63, 69, 506, 171, 172; 422/82.08
See application file for complete search history.

(56) References Cited

U.S. PATENT DOCUMENTS

| 7,332,349 | B2 * | 2/2008 | Yang et al. .................... | 436/507 |
| 2003/0235863 | A1 | 12/2003 | Sklar et al. | |
| 2007/0224628 | A1 | 9/2007 | Gordon et al. | |
| 2007/0233391 | A1 * | 10/2007 | Milstein et al. .................. | 702/19 |

FOREIGN PATENT DOCUMENTS

| EP | 2 000 802 | 3/2007 |
| EP | 2 000 802 | 12/2008 |
| WO | WO 01/09608 | 2/2001 |
| WO | WO 02/080968 | 10/2002 |
| WO | WO 03/012047 | 2/2003 |
| WO | WO 2007/116779 | 10/2007 |

OTHER PUBLICATIONS

Berndt et al. Programmed autologous cleavage of platelet receptors Journal of Thrombosis and Haemostasis, 5 (Suppl. 1): 212-219 (Feb. 7, 2007).*
Qi-Hong Sun et al. Individually Distinct Ig Homology Domains in PECAM-1 Regulate Homophilic Binding and Modulate Receptor Affinity, The Journal of Biological Chemistry 271 (19): 11090-11098 (May 10, 1996)).*
Sun Qu-hong, et al., "Individually distinct Ig homology in PECAM-1 regulate homphilic binding and modulate receptor affinity," Journal of Biological Chemistry, vol. 271, No. 19, pp. 11090-11098, XP002499372 ISSN: 0021-9258 abstract p. 11090, col. 2, paragraph 4, 1998.
Prevost, Jay M., et al., "Granulocyte-macrophage colony-stimulating factor (GM-CSF) and inflammatory stimuli up-regulate secretion of the soluble GM-CSF receptor in human monocytes:Evidence for ectodomain shedding of the cell surface GM-CSF receptor alpha subunit." Journal of Immunology, vol. 169, No. 10, Nov. 15, 2002, pp. 5679-5688, XP002499371 ISSN: 0022-1767.
Serebruany V.L., et al., "Effect of thrombolytic therapy on platelet expression and plasma concentration of PECAM-1 (CD31) in patients with acute myocardial infarction", Arteriosclerosis, Thrombosis, and Vascular Biology, Lippincott Williams & Wilkins, vol. 19, No. 1, Jan. 1, 1999, pp. 153-158, XP002369623 ISSN: 1079-5642 abstract.
Newman, Peter J., et al., "Signal transduction pathways mediated by PECAM-1:new roles for an old molecule in platelet and vascular cell biology." Arteriosclerosis, Theombosis, and Vascular Biology Jun. 1, 2003, vol. 23, No. 6, Jun. 1, 2003, pp. 953-964, XP002515170 ISSN: 1524-4636, the whole document.
Rabesandratana, Herisoa., et al., "Decay-accelerating factor(CD55) and membrane inhibitor of reactive lysis (CD59) are released within exosomes during in vitro maturation of reticulocytes", BLOOD, vol. 91, No. 7, Apr. 1, 1998 pp. 2573-2580, XP002515169 ISSN: 0006-4971 abstract, pp. 2573.

(Continued)

*Primary Examiner* — Gail R Gabel
(74) *Attorney, Agent, or Firm* — Whitham, Curtis, Christofferson & Cook, P.C.

(57) ABSTRACT

The present invention stems from the finding that the extracellular domain of CD31 proteins present on blood leukocytes is shed and released in the circulation as a soluble form of CD31. A method for detecting shed CD31 is further disclosed. The invention therefore relates to a method for detecting a shed ectodomain of a transmembrane protein such as CD31 and to the use of such a method as a diagnostic tool. The invention further provides methods for determining whether a candidate protein is part of a molecular complex.

9 Claims, 6 Drawing Sheets

(56) References Cited

OTHER PUBLICATIONS

Berndt M. C., et al., "Programmed autologous cleavage of platelet receptors", Journal of Thrombosis and Haemostasis-State of the Art 2007; XXI Congress of The International Society of Thrombosis and Haemostasis 200707 GB, vol. 5, No. SUPPL. 1, Jul. 2007, pp. 212-219, XP002546755 abstract.

Watkins, N. A., et al., "Definition of novel GP6 polymorphisms and major difference in haplotype frequencies between populations my combination of in-depth exon resequencing and genotyping with tag single nucleotide polymorphisms," Journal of Thrombosis and Haemostasis:Jun. 2006, vol. 4, No. 6, Jun. 2006, pp. 1197-1205, XP002546756 ISSN: 1583-7933, The whole document.

Wei, H., et al., "Platelet-endothelial cell adhesion molecule-1 gene polymorphism and its soluble level are associated with severe coronary artery stenosis in Chinese Singaporean," Clinical Biochemistry, Pergamon Press, XX, vol. 37, No. 12, Dec. 1, 2004, pp. 1091-1097, XP004675933, ISSN: 0009-9120. abstract.

Database Medline US National Library of Medicine (NLM), Bethesda, MD, US, Mar. 2008, Liu Xin-Guang et al., "Determination of platelet-associate autoantibodies against platelet-specific receptors by cytometric bead array and its clinical application in idiopathic thrombocytopenic purpura." XP002515171 abstract & Zhonghua Xue Ye Xue Za Zhi=Zhonghua Xueyexue Zazhi Mar. 2008, vol. 29, No. 3, pp. 175-178.

Minagar, A., et al., "Plasma from MS patients in exacerbation induces shedding of PECAM-1 from cultured cerebral microvascular endothelial cells (CMVEC)," Abstracts of the Society for Neuroscience, Society for Neuroscience, Washington, DC, US, vol. 26, No. 1-2 Nov. 5, 2000, XP009106475. ISSN: 0190-5295. The whole document.

\* cited by examiner

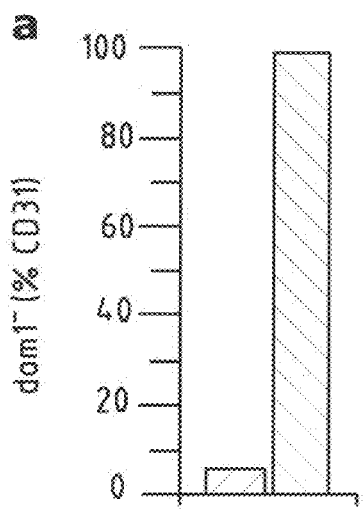
FIG.2
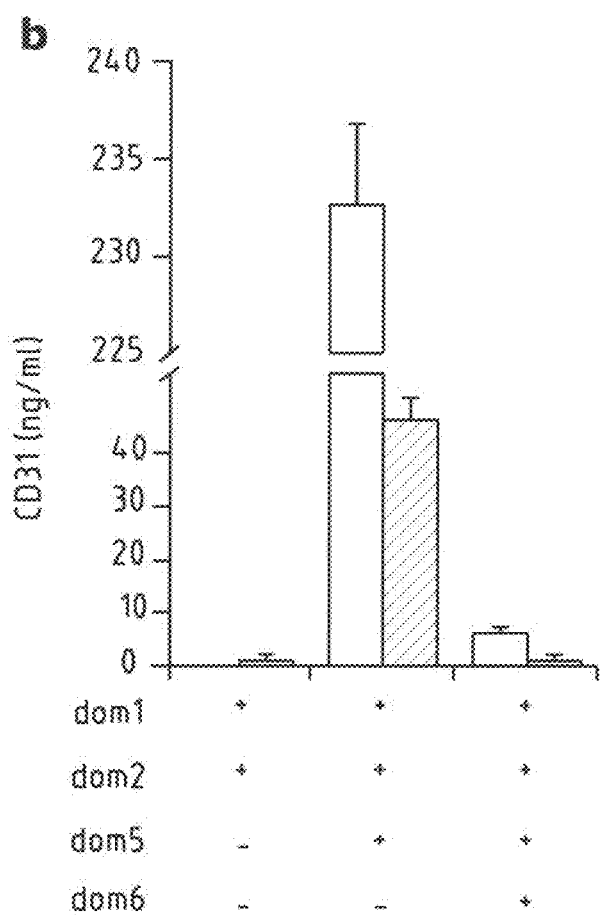

DETECTION OF SHED CD31, DIAGNOSIS OF ATHEROTHROMBOSIS AND AUTOIMMUNE DISORDERS, AND METHODS FOR ANALYZING SIGNALING PATHWAYS

CROSS-REFERENCE TO RELATED APPLICATIONS

This application is a 371 of International Application Number PCT/EP2009/058220 filed Jun. 30, 2009 which is incorporated herein by reference.

FIELD OF THE INVENTION

The present invention stems from the finding that the extracellular domain of CD31 proteins present on blood leukocytes is shed and released in the circulation as a soluble form of CD31. A method for detecting shed CD31 is further disclosed. The invention therefore relates to a method for detecting a shed ectodomain of a transmembrane protein such as CD31 and to the use of such a method as a diagnostic tool. The invention further provides methods for determining whether a candidate protein is part of a molecular complex.

BACKGROUND

CD31 (PECAM-1)

Immune responses can be controlled by inhibitory immune receptors among which CD31 (PECAM-1), which is expressed exclusively and constitutively on cells at the blood-vessel interface.

CD31 consists of a single chain molecule comprising 6 Ig-like extracellular domains, a short transmembrane segment and a cytoplasmic tail containing two ImmunoTyrosine-based Inhibitory Motif (ITIM)s. The structure of CD31 is shown in the table below.

| Domain | Position on SEQ ID No: 1 |
| --- | --- |
| Signal peptide | 1 to 27 |
| Extracellular domain | 28 to 601 |
| First Ig-like extracellular domain | 34 to 121 |
| Second Ig-like extracellular domain | 145 to 233 |
| Third Ig-like extracellular domain | 236 to 315 |
| Fourth Ig-like extracellular domain | 328 to 401 |
| Fifth Ig-like extracellular domain | 424 to 493 |
| Sixth Ig-like extracellular domain | 499 to 591 |
| Juxta-membrane domain | 592 to 601 |
| Transmembrane domain | 602 to 620 |
| Cytoplasmic domain | 621 to 738 |

The consequent putative immunoregulatory properties of CD31 are supported by the fact that CD31 signaling drives mutual repulsion of blood leukocytes and modulates the balance between inhibitory and stimulatory signals of both innate and adaptive immune cells. Mechanical engagement of the distal Ig-like extracellular domains of CD31 induces outside-in inhibitory signaling triggered by the phosphorylation of its ITIMs, and the recruitment and activation of SH2-containing phosphatases.

Zehnder et al. (1995, Blood. 85(5):1282-8) identified a CD31 antibody that inhibited the mixed lymphocyte reaction (MLR) in a specific and dose-dependent manner. They further found that a CD31 peptide corresponding to the epitope of this antibody, i.e. to the 23 membrane-proximal amino acids of CD31, strongly inhibited the MLR. They hypothesized that the 23 membrane-proximal amino acids of CD31 is a functionally important region, and that the CD31 peptide interferes with lymphocyte activation by competing for binding epitopes. However, Zehnder et al. failed to teach whether CD31-mediated signaling is activated or inhibited by the CD31 peptide.

Chen et al. (1997, Blood. 89(4):1452-9) showed that this peptide delayed onset of graft-versus-host disease (GVHD) and increased long-term survival in a murine model of the disease. They hypothesized that the CD31 peptide inhibits a common pathway in T-cell activation. Again, Chen et al. failed to elucidate the role played by the CD31 peptide in T-cell activation. In particular, these previous works did not assess the putative effect of the peptide on the CD31 signaling cascade and more precisely on the phosphorylation state of the CD31 ITIMs.

For a yet unknown mechanism, CD31 is "lost" on certain circulating lymphocytes. Its loss is observed upon lymphocyte activation and it has been recently shown that the absence of lymphocyte CD31 signaling, in turn, heightens the pathologic immune responses involved in the development of atherothrombosis.

A soluble form of CD31, due to a variant transcript lacking the transmembrane segment, has also been reported and therefore it is currently thought that the individual amount of circulating CD31 is genetically determined. Consequently, a number of previous studies have attempted to find a correlation between plasma levels of soluble CD31 and the risk of atherothrombosis or other autoimmune diseases. However, independently of the specific genetic polymorphisms analyzed, data showed a broad range of plasma CD31 values and the results of these different studies were contradicting.

There is therefore a need for better understanding the biological function of CD31. This would allow the provision of better tools for the diagnosis of diseases linked with T-cell activation such as thrombotic and autoimmune disorders.

Methods for Analyzing Signaling Pathways

Three different assays are currently available for analyzing signaling pathways: co-immunoprecipitation followed by Western Blot (co-IP/WB), the Cellular Activation of Signaling ELISA assay (CASE) and the CBA Flex set (BD) assay.

In the co-IP/WB assay, cells are lysed and a protein extraction is first carried out. The studied protein is then co-immunoprecipitated with proteins with which it is associated and a 2D electrophoresis is carried out. Finally, the membrane obtained after the Western Blot is hybridized with a labelled antibody and the signal is detected. It is thus a time-consuming assay. The membrane may be deshybridized and rehybridized with another labelled antibody, but no more than four times. Thus only four parameters may be analyzed with a single sample/membrane. In addition, the co-IP/WB assay is a qualitative but not a quantitative assay. Finally, the skilled in the art must perform two separate co-IP/WB assays if he wishes to compare proteins associated with the studied protein in a phosphorylated state with those associated with the studied protein in an unphosphorylated state.

The CASE (Superarray) and Phosphlow (BD) assays are simpler and more rapid than the co-IP/WB assay since the labelled antibody is added to a sample comprising permeabilized but not lysed cells. In addition, no blotting is needed. The antibodies are labelled with a fluorophore (Phosphlow) or detected via an enzyme (CASE), the activity of which can easily be measured. However, these assays do still not allow analyzing many parameters with a single sample since only a limited number of enzymes are available. In addition, both assays are much less specific than the co-IP/WB assay since the studied molecule is not captured and therefore one cannot determine the interaction between the different molecules of the signaling pathway. The Phosphlow and CASE assays only allow determining which molecules of a given signaling pathway are present in a cell, or present in a phosphorylated state in the cell.

The CBA Flex set (BD) assay allows simultaneous determination of multiple signaling molecules but fails to allow the analysis of molecular complexes, and therefore, the determination of specific receptor-dependent signaling cascades is impossible.

There is therefore a need for improved methods for analyzing signaling pathways, which combines the respective advantages of co-IP/WB, Phosphlow/CASE and CBA Flex set.

DESCRIPTION OF THE INVENTION

In this context, it has surprisingly been found that the assumed loss of CD31 on activated/memory T lymphocytes is actually incomplete and results from shedding of CD31 between the $5^{th}$ and the $6^{th}$ extracellular Ig-like domains. The shed extracellular domain of CD31 (further referred to as "shed CD31") is then released into the circulation, where it is present together with a soluble splice variant of CD31.

In addition, it has been shown that a high risk of atherothrombosis is linked with the increase of the shed CD31 and decrease of the splice variant CD31 in the circulation, and not with the total level of the circulating CD31.

This finding led to the provision of a powerful diagnostic tool. Indeed, since tests that were commercially available so far detected plasma CD31 through the use of antibodies directed to CD31 domains 1 to 5, they could not discriminate between the soluble splice variant of CD31 (containing all the 6 extracellular Ig-like domains) and the shed form of CD31 (containing domains 1 to 5 only). On the other hand, the subtractive method described herein allows discriminating between the two forms of soluble CD31 and precisely quantify the proportion of each of them in a biological sample.

It has been further found that this subtractive method can be adapted in order to analyze soluble forms of other transmembrane proteins than CD31, and to analyze molecular complexes and signaling pathways, e.g. to determine whether a signaling pathway is activated or not, and/or to determine whether a candidate protein is part of a molecular complex.

The invention therefore provides methods for detecting and/or quantifying a shed ectodomain of a transmembrane protein, methods for diagnosing whether an individual suffers from a thrombotic or an autoimmune disorder, diagnostic kits, methods for determining whether a signaling pathway is activated, and methods for determining whether a candidate molecule is part of a molecular complex as further described herein.

The methods according to the invention have many advantages compared to prior art methods such as detection of soluble forms by ELISA. Firstly, they can be infinitely replicated. Indeed, each bead represents an individual test unit, and the number of acquired beads corresponds to the number of replicates. ELISA tests are usually carried out in duplicate or triplicate. However, with the method according to the invention, at least 300 replicates (i.e. cytometric beads) can be acquired simultaneously. Secondly, the methods of the invention are not time-consuming since they can be carried out in about 30 minutes. Thirdly, the quantity of starting material (i.e. of biological sample) that is needed is very low (about 5 µg). Fourthly, several different soluble forms can be detected simultaneously within the same biological sample. Finally, the methods of the invention are more sensitive than ELISA due to the extended range allowed by fluorescent versus colorimetric methods.

Detection of Shed Ectodomains

A method allowing differentiating between different soluble isoforms of a protein has been developed. This method is based on the simultaneous use of antibodies labelled with cytometric beads and of fluorescently-labelled antibodies. The labelled antibodies are then detected by flow cytometry. Briefly, the sample comprising the soluble isoforms is contacted with a first labelled antibody (referred to as the "capture antibody" or the "signaling antibody") that binds to all soluble isoforms to be analyzed. The sample is also contacted with labelled "discriminating antibodies" that only bind to some of the soluble isoforms. The sample is then analyzed by flow cytometry and the proportion of each of the isoforms in said sample is calculated.

Therefore, the invention provides a method for detecting a shed ectodomain of a transmembrane protein among soluble forms of said transmembrane protein in a biological sample, wherein said soluble forms include a soluble splice variant of said transmembrane protein and optionally said shed ectodomain, which comprises the steps of:

a) providing a first type of bead linked to an antibody which specifically binds to an epitope located in a region that is present both on said shed ectodomain and on said splice variant;

b) providing at least a second type of bead linked to an antibody which specifically binds to an epitope located in a region that is either present on said shed ectodomain and absent from said splice variant, or present on said splice variant and absent from said shed ectodomain;

c) providing a fluorescently-labelled ligand which specifically binds to a region that is present both on said shed ectodomain and on said splice variant;

d) contacting said antibodies with a biological sample likely to contain said soluble forms of said transmembrane protein;

e) for each type of bead, measuring the signal obtained with said florescent label by flow cytometry; and f) comparing the signal obtained for each type of bead.

wherein a difference in the signals measured at step (e) indicates that the biological sample comprises said shed ectodomain. In a preferred embodiment, the biological sample is first contacted with the bead-linked antibodies, the beads are then recovered and contacted with the fluorescently-labelled ligand.

In the above method, the shed ectodomain is detected using one single fluorescently-labelled ligand as a signaling ligand and at least two types of bead-linked antibodies as discriminating antibodies.

Alternatively, the shed ectodomains may be detected using one type of bead-linked ligand as a capture ligand and at least two fluorescently-labelled antibodies as discriminating antibodies.

Such a method for detecting a shed ectodomain of a transmembrane protein among soluble forms of said transmembrane protein in a biological sample, wherein said soluble forms include a soluble splice variant of said transmembrane protein and optionally said shed ectodomain, comprises the steps of:

a) providing a bead linked to a ligand which specifically binds to a region that is present both on said shed ectodomain and on said splice variant;

b) providing a first type of fluorescently-labelled antibody which specifically binds to an epitope located in a region that is present both on said shed ectodomain and on said splice variant;

c) providing at least a second type of fluorescently-labelled antibody which specifically binds to an epitope located in a region that is either present on said shed ectodomain and absent from said splice variant, or present on said splice variant and absent from said shed ectodomain;

d) contacting said antibodies with a biological sample likely to contain said soluble forms of said transmembrane protein;

e) for each fluorescently-labelled antibody, measuring the signal obtained with said florescent label by flow cytometry; and f) comparing the signal obtained for each fluorescently-labelled antibody;

wherein a difference in the signals measured at step (e) indicates that the biological sample comprises said shed ectodomain. In this method, each type of fluorescently-labelled antibody is labelled with a different label. Thus the label of the second type of fluorescently-labelled antibody is different from the label of the first type of fluorescently-labelled antibody. In the frame of this method, the bead is preferably not fluorescently labelled. In a preferred embodiment, the biological sample is first contacted with the bead-linked ligand, the beads are then recovered and contacted with the fluorescently-labelled antibodies.

The above methods for detecting a shed ectodomain of a transmembrane protein among soluble forms of said transmembrane protein in a biological sample may further comprise the step of calculating the proportion, percentage and/or amount of said soluble forms that corresponds to said shed ectodomain, and/or the step of comparing the measured signals with those obtained with at least one biological sample comprising known amounts of said shed ectodomain and of said soluble splice variants, and/or the step of calculating the ratio of shed ectodomain (or spliced form) to soluble forms (i.e. all soluble isoforms or "total soluble forms").

As used herein, the term "bead" refers to a cytometric bead for use in flow cytometry. In the method according to the invention, different types of beads refer to beads distinguishable from each other. Such beads may for example correspond to BD™ Cytometric Beads commercialized by BD Biosciences (San Jose, Calif.). Beads are well-known in the art and are further described below.

Flow cytometers enable the characterization of particles on the basis of light scatter and particle fluorescence. In a flow cytometer, particles are individually analyzed by exposing each particle to an excitation light, typically one or more lasers, and the light scattering and fluorescence properties of the particles are measured. Particles, such as molecules, analyte-bound beads, individual cells, or subcomponents thereof, typically are labelled with one or more spectrally distinct fluorescent dyes, and detection is carried out using a multiplicity of photodetectors, one for each distinct dye to be detected. Flow cytometers are commercially available from, for example, BD Biosciences (San Jose, Calif.). Early in the development of flow cytometry, it was recognized that various types of ligand binding assays could be carried out using beads (also referred to as microparticles) coated with one member of a binding pair. The coated beads and reporters are incubated with a sample containing (or suspected of containing) the analyte of interest to allow for the formation of bead-analyte-reporter complexes. Analysis by flow cytometry enables both detecting the presence of bead-analyte-reporter complexes and simultaneously measuring the amount of reporter fluorescence associated with the complex as a quantitative measure of the analyte present in the sample. It was also recognized early in the development of flow cytometry that the simultaneous analysis of multiple analytes in a sample could be carried out using a set of distinguishable beads, each type of bead coated with a unique analyte-specific binding agent. The bead set and fluorescently labelled reporter reagents, one for each species of analyte to be detected, are incubated with a sample containing the analytes of interest to allow for the formation of bead-analyte-reporter complexes for each analyte present, and the resulting complexes are analyzed by flow cytometry to identify and, optionally, quantify the analytes present in the sample. Because the identity of the analyte bound to the complex is indicated by the identity of the bead, multiple analytes can be simultaneously detected using the same fluorophore for all reporter reagents.

A number of methods of making and using sets of distinguishable microparticles have been described in the literature. These include beads distinguishable by size, wherein each size microparticle is coated with a different target-specific antibody (see e.g. Fulwyler and McHugh, 1990, Methods in Cell Biology 33:613-629), beads with two or more fluorescent dyes at varying concentrations, wherein the beads are identified by the levels of fluorescence dyes (see e.g. European Patent No. 0 126,450), and beads distinguishably labelled with two different dyes, wherein the beads are identified by separately measuring the fluorescence intensity of each of the dyes (see e.g. U.S. Pat. Nos. 4,499,052 and 4,717,655).

Both one-dimensional and two-dimensional arrays for the simultaneous analysis of multiple analytes by flow cytometry are available commercially. Examples of one-dimensional arrays of singly dyed beads distinguishable by the level of fluorescence intensity include the BD™ Cytometric Bead Array (CBA) (BD Biosciences, San Jose, Calif.) and CytoPlex™ Flow Cytometry microspheres (Duke Scientific, Palo Alto, Calif.). An example of a two-dimensional array of beads distinguishable by a combination of fluorescence intensity (five levels) and size (two sizes) is the QuantumPlex™ microspheres (Bangs Laboratories, Fisher, Ind.). An example of a two-dimensional array of doubly-dyed beads distinguishable by the levels of fluorescence of each of the two dyes is described in Fulton et al. (1997, Clinical Chemistry 43(9): 1749-1756).

As used herein, the term "specifically binding" has its usual meaning within the art. The fact whether a molecule specifically binds to another molecule is generally determined by a competitive binding assay.

The biological sample may for example correspond to plasma, blood or urine. The biological sample preferably corresponds to plasma. Most preferably, the biological sample is obtained from an individual suffering from or at risk of suffering from a thrombotic or an autoimmune disorder.

By "ligand" is meant a natural ligand, an antibody or an aptamer. The ligand preferably is an antibody that specifically binds to an epitope located in a region that is present both on the shed ectodomain and on the splice variant.

As used herein, the term "antibody" refers both to monoclonal and to polyclonal antibodies. The antibody is preferably a monoclonal antibody. However, it may also correspond to a polyclonal antibody.

The fluorescently-labelled ligand and/or antibody may be labelled with any fluorescent compound known in the art such as e.g. FITC (FL1), PE (FL2), fluorophores for use in the blue laser (e.g. PerCP, PE-Cy7, PE-Cy5, FL3 and APC or Cy5, FL4), fluorophores for use in the red, violet or uv laser (e.g. Pacific blue, pacific orange). Optimized methods include different emission spectra for the beads and the detecting antibodies. The antibody is preferably directly labelled. However, it may also be indirectly labelled, especially when the antibody is a polyclonal antibody.

As used herein, the term "shed ectodomain of a transmembrane protein" refers to an extracellular portion of a transmembrane protein which has been cleaved by proteolytic processing. Examples of transmembrane proteins for which a shed ectodomain exist include but are not limited to L-selectin (Asimakopoulos et al., Perfusion, 2000. 15(6): p. 495-9), ICAM-1 (Becker, et al., J Immunol, 1991. 147(12): p. 4398-401), VCAM-1 (Garton et al., SJ Biol Chem, 2003. 278(39): p. 37459-64), VCAM-1 receptor (Belgore et al., Am J Cardiol, 2001. 87(6): p. 805-7, A9), P-selectin (Dole et al., Thromb Haemost, 2007. 98(4): p. 806-12), CD40 (Contin et al. J Biol Chem, 2003. 278(35): p. 32801-9), CD23 (Gu et al., Blood, 1998. 92(3): p. 946-51), CD21 (Fremeaux-Bacchi et al., Int Immunol, 1998. 10(10): p. 1459-66), HLA-E (Derre et al., J Immunol, 2006. 177(5): p. 3100-7), NgR (Ahmed et al., Faseb J, 2006. 20(11): p. 1939-41), Hepatocyte growth factor (Wajih et al. Circ Res, 2002. 90(1): p. 46-52), IL-6R (Franchimont et al., Arthritis Rheum, 2005. 52(1): p. 84-93), TNFa (Fabris et al., Clin Exp Immunol, 1999. 117(3): p. 556-60), IL-4R (Silvestri et al., Osteoarthritis Cartilage, 2006. 14(7): p. 717-9), IL-1R (Beck et al., Mol Immunol, 1994. 31(17): p. 1335-44), transferring receptor (Chitambar et al., Blood, 1991. 78(9): p. 2444-50) and the common gamma chain of immunoglobulins (Meissner et al., Blood, 2001. 97(1): p. 183-91).

In a preferred embodiment according to the invention, the transmembrane protein is CD31.

As used herein, the term "CD31" refers to the platelet/endothelial cell adhesion molecule also referred to as CD31 antigen or PECAM-1. The protein may be of any origin, preferably of mammalian origin, and most preferably of human origin. In human, the gene coding for CD31 is located at locus 17q23. The sequence of human wild-type CD31 is shown as SEQ ID NO: 1. However, the invention also relates to allelic variants thereof, and to the homologs thereof in other species.

As shown in FIG. 5 and in the Sequence Listing for SEQ ID NO: 1 (human CD31), the CD31 protein comprises six extracellular immunoglobulin-like (Ig-like) domains. In addition, CD31 exists not only as a transmembrane protein but also as a soluble splice variant comprising the six extracellular Ig-like domains (see Goldberger et al. 1994. J Biol Chem 269: 17183-17191).

It has unexpectedly been found that soluble forms of CD31 include a shed ectodomain comprising the $1^{st}$, $2^{nd}$, $3^{rd}$, $4^{th}$ and $5^{th}$ extracelluar Ig-like domains. Thus the $6^{th}$ extracellular Ig-like domain is present in the soluble splice variant but absent from the shed ectodomain.

Therefore, a preferred embodiment of the invention relates to a method for detecting a shed ectodomain of CD31 among soluble forms of CD31 in a biological sample wherein at least two discriminating antibodies are used, one specifically binding to an epitope located in either of the first five extracellular immunoglobulin-like domain of CD31, and another one specifically binding to an epitope located in the sixth extracellular immunoglobulin-like domain of CD31. The capture or signaling ligand may for example specifically bind to the first and/or second extracellular immunoglobulin-like domains of CD31. the capture of signaling ligand is preferably a capture or signaling antibody, which may for example specifically bind to an epitope located in the first and/or second extracellular immunoglobulin-like domains of CD31.

Such antibodies are well-known in the art and may for example correspond to any one of the antibodies listed in the HLDA Antibody Database (see world wide web page 99.mh-hannover.de/aktuelles/projekte/hlda7/hldabase/CD31.htm).

As used herein, the term "epitope located in the sixth extracellular immunoglobulin-like domain of CD31" refers to an epitope located within amino acids 499 to 601 of SEQ ID NO: 1, i.e. within the sixth extracellular immunoglobulin-like domain of CD31 (amino acids 499 to 591 of SEQ ID NO: 1) and/or within the juxta-membrane region (amino acids 592 to 601 of SEQ ID NO: 1). Preferably, said epitopes are located within amino acids 499 to 591, 524 to 601 or 524 to 538 of SEQ ID NO: 1. In a preferred embodiment, the antibody which specifically binds to an epitope located in the sixth extracellular immunoglobulin-like domain of CD31 corresponds to the PECAM 1.2 antibody (Invitrogen, San Diego, Calif.), the PECAM1.1 antibody, or the HC1/6 antibody (Serotec, Kidlington, UK). The PECAM 1.2 antibody has been described e.g. in Yan et al. (Cell Adhes Commun 3:45-66).

As used herein, the term "epitope located in either of the first five extracellular immunoglobulin-like domain of CD31" refers to an epitope located within amino acids 28 to 493 of SEQ ID NO: 1, most preferably within amino acids 34 to 493 of SEQ ID NO: 1. In preferred embodiments according to the invention, said epitope is located in the fifth extracellular immunoglobulin-like domain of CD31, or in the first and/or second extracellular immunoglobulin-like domain of CD31.

As used herein, the term "epitope located in the fifth extracellular immunoglobulin-like domain of CD31" refers to an epitope located within amino acids 424 to 493 of SEQ ID NO: 1. Preferably, said epitopes are located within amino acids 448 to 470 of SEQ ID NO: 1. In a preferred embodiment, the antibody which specifically binds to an epitope located in the fifth extracellular immunoglobulin-like domain of CD31 corresponds to the MEM-05 antibody (Zymed Laboratories, South San Francisco, Calif.).

As used herein, the term "epitope located in the first and/or second extracellular immunoglobulin-like domain of CD31" refers to an epitope located within amino acids 34 to 233 of SEQ ID NO: 1. An epitope located in the first extracellular immunoglobulin-like domain of CD31 is preferably located within amino acids 49 to 68 of SEQ ID NO: 1. An epitope located in the first extracellular immunoglobulin-like domain of CD31 is preferably located within amino acids 166 to 187 of SEQ ID NO: 1. In a preferred embodiment, the antibody which specifically binds to an epitope located in the first two extracellular immunoglobulin-like domains of CD31 corresponds to the WM59 antibody (domain 2, BD, San Jose, Calif.), to the JC70A antibody (domain 1, DAKO, Glostrup, Denmark), or to the 9G11 antibody (domain 1, R&D systems, Minneapolis, USA). The WM59 and JC70A antibodies have been described e.g. in Fawcett et al. (J Cell Biol 128:1229-1241).

Said soluble forms of the transmembrane protein may include additional soluble forms corresponding to e.g. additional soluble splice variants, additional shed ectodomains, or to variants generated by proteolytic processing. When the soluble forms include at least three soluble forms, more than two discriminating antibodies may be used. Within this embodiment, the discriminating antibodies are chosen in such a way as to discriminate between the soluble forms, and the capture or signaling antibody specifically binds to an epitope located in a region that is present on all said soluble forms.

Data from five plasma samples showed that most circulating shed CD31 comprises Ig-like domains 1 to 5. However, Ig-like domain 5 could be absent in up to 16% of plasma CD31, indicating that more that one cleavage site may exist in the extracellular CD31 domains. Therefore, a more accurate test for differentiating between all soluble forms of CD31 would include also detection of Ig-like domain 1, in addition to detection of Ig-like domains 5 and 6 of CD31. Thus the method for detecting a shed ectodomain of CD31 among soluble forms of CD31 in a biological sample may comprise the use of three discriminating antibodies, which specifically binds to epitopes located in the first and/or second extracellular immunoglobulin-like domain of CD31, in the fifth extracellular immunoglobulin-like domain of CD31, and in the sixth extracellular immunoglobulin-like domain of CD31, respectively. In this embodiment, the capture or signaling antibody must specifically bind to an epitope located in the first and/or second extracellular immunoglobulin-like domains of CD31.

The method for detecting of a shed ectodomain of CD31 may further comprise the step of calculating the proportion, percentage and/or amount of said soluble forms that corresponds to said shed ectodomain of CD31, and/or the step of comparing the measured signals with those obtained with at least one biological sample comprising known amounts of said shed ectodomain and of said soluble splice variants. The calculation can for example be performed as described e.g. in the paragraph entitled "subtractive measurement of soluble CD31" in Example 1. The method for detecting of a shed ectodomain of CD31 preferably comprises the step of calculating the ratio of shed ectodomain to total soluble forms, i.e. the ratio of shed CD31 to all soluble isoforms (soluble isoform comprising domains 1-6, soluble isoform comprising domains 1-5, and soluble isoform comprising domains 1-2).

FIG. 4 illustrates a method in accordance with the invention for the detection and quantification of the shed ectodomain of CD31. Three types of beads, linked to antibodies specifically binding to epitopes located in the $1^{st}$, the $5^{th}$ or the $6^{th}$ extracellular Ig-like domain respectively, are used. The fluorescently labelled antibody specifically binds to an epitope located on the $1^{st}$ and $2^{nd}$ extracellular Ig-like domains. A simple subtractive calculation based on measurement of the intensity of the signal obtained for each bead allows quantifying the respective proportion of each of the soluble forms of CD31:

Soluble isoform comprising domains 1-6=$aCD31_{d6}$
Soluble isoform comprising domains 1-5=$aCD31_{d5}$−$aCD31_{d6}$
Soluble isoform comprising domains 1-2=$aCD31_{d1}$−($aCD31_{d5}$+$aCD31_{d6}$)

The above methods aim at detecting shed ectodomains which are soluble in a biological fluid. However, these methods may be adapted to detect a shed isoform of a transmembrane protein (e.g. $CD31^{shed}$) on a cell expressing said transmembrane protein. In that case, the discriminating antibodies specifically bind to epitopes that are located either in a region that is present both on the shed isoform and on the full-length transmembrane protein (e.g. Ig-like domain 6), or in a region that is present either on the shed isoform or on the full-length transmembrane protein (e.g. Ig-like domains 1-2). This aspect of the invention is illustrated for CD31 by Example 2, FIG. 1 and FIG. 2a.

In another preferred embodiment according to the invention, the transmembrane protein is GPVI.

As used herein, the term "GPVI" refers to the platelet glycoprotein VI. The protein may be of any origin, preferably of mammalian origin, and most preferably of human origin. The sequence of human wild-type GPVI is shown in SwissProt Acession No. Q9HCN6. The term "GPVI" encompasses the wild-type sequence, variants thereof such as splice and allelic variants, and homologs thereof in other species.

The spliced form of GPVI comprises the cytoplasmic tail and can therefore be detected using specific antibodies such as those raised against a maltose-binding protein (MBP)-GPVI cytoplasmic tail fusion protein (see e.g. Suzuki-Inoue et al. J Biol. Chem. 2002 277:21561-66). On the contrary, the shed form of GPVI comprises all the ectodomains. Example of suitable anti-ectodomain antibodies include clones 11A12, 6B12, 3j24.2 and 9O12.2 disclosed in WO/2001/000810). The GPVI natural ligand convulxin binds both to the spliced form and to the shed form of GPVI.

Therefore, the detection of shed ectodomains of GPVI can be carried out using can be performed using either:
  anti-tail and anti-ectodomain antibodies linked to different types of beads as discriminating antibodies, and fluorescently labeled convulxin as a signaling ligand, or
  a convulxin-coupled bead as a capture ligand, differently labeled fluorescent anti-tail and anti-ectodomain antibodies as discriminating antibodies.

It is also understood that the above methods may be used for detecting a soluble isoform of a protein even if said soluble form is not a shed ectodomain of a transmembrane protein. The methods according to the inventions can be used for detecting a soluble form of any protein existing as at least two different soluble forms, e.g. existing as two soluble splice variants. In other terms, they allow detecting and distinguishing between different soluble forms of a protein.

The methods according to the invention are illustrated by the specific example of CD31. However, the skilled in the art can easily adapt this method to another protein of his own choice. Depending on the structure of the soluble domains, the skilled in the art will choose antibodies recognizing regions present on or absent from only one of the soluble forms. In addition, the skilled in the art will choose antibodies in such a way as to allow simultaneous binding of several antibodies. Such antibodies can easily be chosen by ascertaining that the antibodies do not recognize overlapping epitopes. Therefore, a preferred embodiment of the invention is directed to a method in which the capture or signaling antibody and the different discriminating antibodies do not cross-compete with each other. Methods for determining whether antibodies cross-compete with each other are well-known in the art and include e.g. the method described by Blanchard et al. (1997, International immunology, 9(12): 1775-1784).

In a specific embodiment, methods comprising the step of fragmenting (e.g. by enzymatic digestion) the proteins that are present in the biological sample are excluded from the scope of the present invention.

The above methods for detecting shed ectodomains and/or shed isoforms of a transmembrane protein find use both in analytical and diagnostic applications. Some of the diagnostic applications are described in more details in the paragraph herebelow.

Diagnostic Methods and Drug Monitoring

It has been found that a high risk of atherothrombosis is linked with the presence of shed CD31 in the circulation, and not with the amount of total circulating soluble CD31.

The invention therefore provides a method for diagnosing whether an individual suffers, or is at risk of suffering, from a thrombotic or an autoimmune disorder, which comprises the step of detecting a shed ectodomain of CD31 in a biological sample of said individual, wherein the presence of said shed ectodomain of CD31 indicates that said individual suffers from or is at risk of suffering from said thrombotic or autoimmune disorder. Where shed ectodomain of CD31 is detectable, the method may further comprise the step of calculating the ratio of shed ectodomain to total soluble forms. Indeed, it has been found that this ratio has a very good predictive value (see Example 7).

Based on this diagnosis, an appropriate treatment regimen may be designed for said individual. Preferably, said shed ectodomain of CD31 comprises the $1^{st}$, $2^{nd}$, $3^{rd}$, $4^{th}$ and $5^{th}$ extracellular Ig-like domains but lacks the $6^{th}$ extracellular Ig-like domain.

As used throughout the present specification, the term "thrombotic disorder" includes but is not limited to atherothrombosis, atherosclerosis, acute coronary syndrome, ischemic stroke, peripheral arterial disease and abdominal aortic aneurysm. Preferably, the thrombotic disorder is atherothrombosis.

As used throughout the present specification, the term "autoimmune disorder" includes but is not limited to rheumatoid arthritis (RA), spondyloarthritis, multiple sclerosis (MS), inflammatory bowel disease (IBD), systemic lupus erythematodes (SLE), Graves' disease and diabetes mellitus.

The detection of said shed ectodomain of CD31 may be performed according to any method known in the art. It may for example be detected by one of the methods described in the above paragraph. Alternatively, the detection may be performed by an ELISA assay. It is however preferred to detect the shed CD31 ectodomain according to a method according to the invention, since such methods are easier to set up, more rapid and more sensitive.

The biological sample may for example correspond to plasma, blood or urine. The biological sample preferably corresponds to plasma.

The diagnostic method in accordance with the invention may be repeated at least at two different points in time in order to monitor the progression of a thrombotic or an autoimmune disorder in the individual and/or to assess the severity of said disorder in said individual, and/or to monitor the response of the individual to a drug.

As used herein, events occurring at "a different (or later) point in time" refer to events occurring at an interval of at least 1 hour. Preferably, the events occur at an interval of at least 6 hours, 12 hours, 1 day, one week, two weeks or one month.

The invention also pertains to the use of an antibody which specifically binds to an epitope located in the sixth extracellular immunoglobulin-like domain of CD31 for diagnosing whether an individual suffers, or is at risk of suffering, from a thrombotic or autoimmune disorder.

The invention further provides a method for diagnosing whether an individual suffers, or is at risk of suffering, from atherothrombosis, which comprises the steps of:
a) providing a biological sample of said individual;
b) detecting the shed ectodomain of CD31, for example according to any of the methods described in the above paragraph entitled "detection of shed ectodomains", in said biological sample; and
c) correlating the result of step (a) with a risk of suffering from atherothrombosis;
wherein the presence of said shed ectodomain of CD31 in said biological sample indicates that said individual suffers from or is at risk of suffering from atherothrombosis. Preferably, said shed ectodomain of CD31 comprises the $1^{st}$, $2^{nd}$, $3^{rd}$, $4^{th}$ and $5^{th}$ extracellular Ig-like domains but lacks the $6^{th}$ extracellular Ig-like domain.

The presence of at least 50%, 60%, 65%, 70%, 75%, 80%, 90% or 95% of shed ectodomain in the soluble forms of CD31 indicates that said individual suffers from or is at risk of suffering from a thrombotic or an autoimmune disorder such as e.g. atherothrombosis.

In a preferred embodiment, the amount and/or percentage of shed CD31 in a biological sample of said individual to be diagnosed is compared to the amount and/or percentage of shed CD31 in a biological sample of a healthy individual.

High levels of CD31 soluble splice variants associated with low levels of shed CD31 indicates that the individual to be diagnosed suffers from non specific chest pain, eventually associated with carotid plaques. A slight increase of shed CD31 levels associated with normal or reduced levels of CD31 soluble splice variants indicates that the individual to be diagnosed suffers from atherosclerosis. An important increase of shed CD31 levels associated with undetectable amounts of CD31 soluble splice variants indicates that the individual to be diagnosed suffers from atherothrombosis.

The diagnostic methods in accordance with the invention may be used e.g. to determine whether an individual suffers from a thrombotic or an autoimmune disorder, to assess the severity of a thrombotic or an autoimmune disorder in an individual, to pronostic the risk of major cardiovascular events, such as recurrence of a myocardial infarction, to design a treatment regimen, to monitor the progression of a thrombotic or an autoimmune disorder in a patient, to predict and to monitor the response of a patient to a drug and/or to adjust the treatment of a patient.

When the diagnostic method in accordance with the invention is used to monitor the progression of a disorder, to assess the severity of a disorder, to monitor the response to a drug and/or to adjust the treatment of a patient, it carried out on biological samples taken from a given patient at different points in time. Biological samples may for example be taken each month in order to follow the patient's response to a treatment. Based on these analyses, the treatment may then be adjusted. It may for example be decided to change the drug, or to adjust the dosage of the drug in order to enhance its efficacy and/or minimize the side effects. Such a drug monitoring is especially advisable in long-term treatments, for example when a immunosuppressant compound is administered to a patient. Detecting shed CD31 can be used to monitor the inflammatory response in the patient, and thus to determine the minimal effective dose of drug that can be administered to the patient.

The invention therefore provides a method for monitoring the progression of a thrombotic or an autoimmune disorder, and/or for assessing the severity of a thrombotic or an autoimmune disorder in an individual, and/or for monitoring the response of a patient to a drug comprising the steps of:
a) providing a first biological sample of said patient;
b) detecting shed ectodomains of CD31 in said first biological sample;
c) providing at least one second biological sample of said patient, wherein said at least one second biological sample has been taken from said patient at a later point in time than the first biological sample;
d) detecting shed ectodomains of CD31 in said at least one second biological sample;
e) comparing the results obtained at steps (b) and (d).

Several different biological samples, taken from the same patient at different points in times, may be used at steps (c), (d) and (e). For example, in the frame of a long-term treatment of the patient, biological samples may be taken from the patient at regular intervals (e.g. each month, every two months or twice a year).

Such a method for monitoring the progression of a thrombotic or an autoimmune disorder; and/or to assess the severity of said disorder; and/or for monitoring the response of a patient to a drug may further comprise a step (f) of designing a treatment regimen for said patient based on the results of step (e).

In the frame of drug monitoring, the biological sample of step (a) is preferably taken before onset of the treatment of the patient, and the biological sample of step (c) after onset of the treatment. A decrease of shed CD31 levels measured at step (d) as compared to shed CD31 levels measured at step (b) indicates that the drug is effective for treating said patient.

More specifically, the invention relates to a method for monitoring the response of a patient suffering from a thrombotic or autoimmune disorder to a drug, said method comprising the steps of:
- a) detecting shed ectodomains of CD31 in a biological sample of said patient before and after onset of a treatment of said patient with said drug;
- b) comparing the levels of shed ectodomains of CD31 detected at step (a); and, optionally,
- c) correlating a difference in said levels of shed ectodomains of CD31 with the effectiveness of the drug for treating said patient.

A decrease in the levels of shed ectodomains of CD31 after onset of the treatment compared with the levels of shed ectodomains of CD31 before onset of the treatment indicates that the patient responds to said drug, and that said drug is effective for treating said patient. Preferably, the decrease is of at least 5, 10, 25, 50, 75 or 90%. Conversely, if no significant difference in the levels of shed ectodomains of CD31 is found at step (b), or if an increase in the levels of shed ectodomains of CD31 after onset of the treatment is found at step (b), the patient does not respond to said drug and the drug is not effective for treating said patient.

The invention further pertains to the use of an antibody which specifically binds to an epitope located in the sixth extracellular immunoglobulin-like domain of CD31 for monitoring the progression of a thrombotic or an autoimmune disorder in a patient, and/or for monitoring the response of a patient to a drug.

Diagnostic Kits

The invention also contemplates diagnostic kit comprising:
- a) a fluorescently-labelled antibody that specifically binds to an epitope located in a region that is present both on said shed ectodomain and on soluble said splice variant.
- b) a first type of bead linked to an antibody that specifically binds to an epitope located in a region that is either present on said shed ectodomain and absent from said soluble splice variant, or present on said soluble splice variant and absent from said shed ectodomain; and
- c) a second type of bead linked to an antibody that specifically binds to an epitope located in a region that is present both on a shed ectodomain of a transmembrane protein and on a soluble splice variant of said transmembrane protein.

Such kits can be used, e.g., in the diagnostic methods according to the invention, and/or in drug choice, and/or in drug monitoring.

In a preferred embodiment, the transmembrane protein is CD31. The fluorescently-labelled antibody and the antibody linked to the first type of bead preferably specifically bind to an epitope located in either of the first five extracellular immunoglobulin-like domain of CD31. The antibody linked to the second type of bead preferably specifically binds to an epitope located in the 6$^{th}$ Ig-like domain.

Such a diagnostic kit may for example comprise:
- a fluorescently-labelled antibody specifically binding to an epitope located in the first and/or second extracellular immunoglobulin-like domains of CD31 (e.g. a labelled WM59 antibody, a labeled 9G11 antibody, or a labelled JC70A antibody, DAKO,);
- a first type of bead linked to an antibody which specifically binds to an epitope located in the sixth extracellular immunoglobulin-like domain of CD31 (e.g. the PECAM 1.2 antibody);
- one or both of:
  - i) a second type of bead linked to an antibody which specifically binds to an epitope located in the fifth extracellular immunoglobulin-like domain of CD31 (e.g. the MEM-05, PECAM 1.1 or HC1/6 antibody); and
  - ii) a third type of bead linked to an antibody which specifically binds to an epitope located in the first and/or second extracellular immunoglobulin-like domain of CD31 (e.g. JC70A, 9G11 or WM59 antibody).

In a specific embodiment, the kit comprises a first type of bead linked to the PECAM 1.2. antibody, a second type of bead linked to the MEM-05 antibody, a fluorescently labelled WM-59 antibody (e.g. PE-WM-59), and optionally a third type of bead linked to the JC70A antibody.

Other diagnostic kits according to the invention comprise:
- a) a bead linked to an antibody that specifically binds to an epitope located in a region that is present both on a shed ectodomain of a transmembrane protein and on a soluble splice variant of said transmembrane protein;
- b) a first type of fluorescently-labelled antibody that specifically binds to an epitope located in a region that is either present on said shed ectodomain and absent from said soluble splice variant, or present on said soluble splice variant and absent from said shed ectodomain; and
- c) a second type of fluorescently-labelled antibody that specifically binds to an epitope located in a region that is present both on said shed ectodomain and on soluble said splice variant, wherein the label of said second fluorescently-labelled antibody is different from the label of said first fluorescently-labelled antibody; and, optionally
- d) a third type of fluorescently-labelled antibody that specifically binds to an epitope located in a region that is present both on said shed ectodomain and on soluble said splice variant, wherein the label of said third fluorescently-labelled antibody is different from the label of said first and second fluorescently-labelled antibodies.

In a preferred embodiment, the transmembrane protein is CD31. The second fluorescently-labelled antibody and the antibody linked to the bead preferably specifically bind to an epitope located in either of the first five extracellular immunoglobulin-like domain of CD31. The first fluorescently-labelled antibody preferably specifically binds to an epitope located in the 6$^{th}$ Ig-like domain.

Another preferred embodiment is directed to a kit comprising:
- a bead linked to an antibody specifically binding to an epitope located in the 1$^{st}$ extracellular Ig-like domain (e.g. a Pecam1.3, 9G11 or a JC70A antibody);
- a first type of fluorescently-labelled antibody specifically binding to an epitope located in the 6th extracellular Ig-like domain (e.g. a labelled PECAM 1.2 antibody such as FITC-PECAM 1.2);
- one or both of:
  - a second type of fluorescently-labelled antibody specifically binding to an epitope located in the 1$^{st}$ or 2$^{nd}$ extracellular Ig-like domain (e.g. a labelled WM59 or L133 antibody such as PE-WM59 or PE-L133); and a third fluorescently labeled antibody which specifically binds to an epitope located in the 5$^{th}$ extracellular Ig-like domain (e.g. the MEM-05 or PECAM 1.1 or HC1/6 antibody);

Fluorescently labeled antibody may include fluorophores exited by a blue-laser and emitting in the FITC, PE, PerCP or PE-tandem channels, or excited by a red laser and emitting in the Cy5/APC or APC-tandem channels, or by a violet laser and emitting in the pacific blue or pacific orange channels or by a UV laser and emitting in the Quantum Dot channels);

These kits may additionally comprise other components such as e.g. reagents and/or instructions.

The kits may also comprise samples comprising a known amount of shed ectodomain of CD31 and/or of soluble splice variants, samples from healthy individuals and/or samples from individuals suffering from atherosclerosis or atherothrombosis.

Methods for Analyzing Signaling Pathways

The above methods of detecting shed ectodomains may be adapted for other purposes such as the analysis of protein/protein interaction and of signaling pathway. This method is easier, more rapid and more powerful than co-IP/WB, more specific than CASE/Phosphlow and CBA Flex set, and actually combines the advantages of these techniques.

The invention therefore provides a method of determining whether a candidate molecule is member of a molecular complex which comprises the steps of:
a) providing a bead linked to an antibody that specifically binds to a member of said molecular complex;
b) contacting said bead with a biological sample containing said molecular complex;
c) contacting said beads contacted with the biological sample with at least one type of fluorescently-labelled antibody that specifically binds to said candidate molecule; and
d) detecting the fluorescence by flow cytometry;
wherein:
the detection of a signal at step (d) indicates that said candidate molecule is a member of said molecular complex; and
if more than one type of fluorescently-labelled antibody is used at step (c), said antibodies are labelled with different fluorescent labels.

The method according to the invention allows performing several determinations simultaneously, using the same biological sample. Therefore, the above method may be carried out for at least 2, 3, 4, 5, 6, 7 or 10 candidate molecules simultaneously. In such a case, step (c) comprises contacting said beads contacted with the biological sample with fluorescently-labelled antibodies that specifically bind to each of said at least 2, 3, 4, 5, 6, 7 or 10 candidate molecules. Each of these fluorescently-labelled antibodies is labelled with a fluorescent label that is different from the other fluorescent labels.

The biological sample preferably corresponds to soluble or solubilized molecules, preferably derived from a cell. The biological sample may for example correspond to a cell lysate. A protocol for preparing such a cell lysate is for example described in Example 5. Cells may for example be lysed on ice for 30 minutes with a RIPA buffer containing a cocktail of protease and phosphatase inhibitors. Alternatively, soluble or solubilized molecules may for example be prepared by freezing, thawing and crushing cells.

The above method allows gathering multiple information relating to a given molecular complex and/or a given signaling pathway. As used herein, a "molecular complex" refers to a complex of associated molecules. The molecules may for example correspond to proteins, lipids, sugars or nucleotides. In a preferred embodiment, the molecular complex is a protein complex and the members of said protein complex are proteins.

The method according to the invention allows for example determining the proteins that are associated with a given protein under specific conditions, or determining whether a given protein is phosphorylated or not (by using a fluorescently-labelled antibody specifically recognizing the phosphorylated isoform of the protein). The candidate molecule may thus correspond e.g. to a protein that is associated to the bead-captured member of the molecular complex only under certain conditions, a protein that is phosphorylated only under certain conditions, or to a protein for which it is not known whether it is a member of said molecular complex. The method according to the invention also allows analyzing a complex of glycoproteins and of protoglycans of the extracellular matrix, or a complex of sugars, lipids and proteins involved in thrombus formation.

The antibodies used at step (c) may specifically bind to all isoforms of a protein likely to be member of said molecular complex, or only to a shed, spliced or phosphorylated isoform of said protein.

Alternatively, the antibodies used at step (c) may bind to phosphorylated amino acids such as phosphotyrosin, phosphoserin or phosphothreonin, irrespective of the primary sequence of the protein.

The antibodies used at step (c) may also specifically bind to nucleotides (DNA or RNA sequences, cyclic nucleotides such as AMPc or GMPc), sugars (e.g. sialic acid), lipids involved in signaling pathways (e.g. steroid hormones, inositol, phosphatidylinositol, leukotrienes, prostaglandins, thomboxane, gangliosides, caveolin, ceramides, etc), lipopolysaccharides involved in TLR-mediated signaling, and glycolipids (e.g. galactocerebroside, which is involved in oligodendrocyte signaling).

The molecular complex may include e.g. membrane receptors, extracellular ligands and intracellular proteins such as transduction proteins. Most preferably, the candidate molecule is an intracellular molecule, e.g. an intracellular protein.

Examples of molecular complexes that can be analyzed using this method include those given in the table below. The protein captured with the bead-linked antibody may be any one of the members of the molecular complex.

| Signaling pathway | Membrane associated proteins | Phosphoproteins | Associated intracellular proteins (activator) | Associated intracellular proteins (inhibitor) |
|---|---|---|---|---|
| CD3 signaling (T cell) | CD31, CD3, CD45, CD28, CTLA4, SLAM, CD31 | P56LcK, phosphoITAM of the TCR (CD3ζ) | Zap70, NFkB, ERK, IkBK, RhoA . . . | CsK, PTPase |

| Signaling pathway | Membrane associated proteins | Phosphoproteins | Associated intracellular proteins (activator) | Associated intracellular proteins (inhibitor) |
|---|---|---|---|---|
| IgM signaling (B cell) | IgM, CD19, CD22 | Iga/b ITAM, SYK, GRB2, BTK, PI3K | RAS, IKK, PKCb, RAC | SHP1, SHIP, PTEN, cleaved Notch |
| IL-6R (cytokine signaling) | IL-6R, Gp130 | IL-6 receptor (4 tyrosins) | Jak1, Stat3, Gab, ERK, MAPK | SHP2, SOCS3 |
| b-integrin signaling (cancer research) | Be-integrin, Talin, Paxillin, Fyn, FAK | FAK | a-actinin, GRb2, Ras, Raf1, MEK1/2, ERK1/2 . . . | Sos, PTPase |
| C83 signaling (after shedding) (Alzheimer research) | C83 (after shedding), b-secretase, a-secretase, C99 (left on by b-secretase) APP (on whole molecule) | GSK3 | Cdk5/p25, Cdk5/p35 | |
| FasL signaling (Apoptosis) | FasL, FADD, TRADD, TNF-R1, RIP, Reaper, Caspases, FLIP | | p53, Bax, BCL-2, Apaf-1, MDM2, c-Myc | |

In a preferred embodiment, the member of said molecular complex captured with the bead-linked antibody is CD31.

The fluorescently-labelled antibody may for example correspond to an antibody that specifically binds to a CD31 protein comprising a phosphorylated tyrosine at position 686. Alternatively, the fluorescently-labelled antibody may for example correspond to an antibody that specifically binds to a phosphorylated isoform of an intracellular protein which is part of the CD31 signaling pathway, or to a transduction protein which is part of the CD31 signaling pathway. Such proteins are described e.g. in Newman and Newman (2003 Arterioscler Thromb Vasc Biol 23:953-964) and/or in Newton-Nash and Newman (1999. J Immunol 163:682-688). Such antibodies may for example bind to a CD31 protein comprising the sixth extracellular immunoglobulin-like domain (e.g. PECAM 1.2), a CD31 protein comprising the second extracellular immunoglobulin-like domain (e.g. WM59), CD3, CD28, SHP2, CD45, CTLA4, SLAM, p56LcK, CD3ζ, Zap70, NFkB, ERK, IkBK, RhoA, CsK and PTPase.

The invention further provides a kit for analyzing a molecular complex which comprises:
i) a bead linked to an antibody that specifically binds to a member of said molecular complex; and
ii) at least one type of fluorescently-labelled antibody that specifically binds to another member of said molecular complex.
wherein, if the kit comprises more than one type of fluorescently-labelled antibody, said antibodies are labelled with different fluorescent labels.

More specifically, the invention further provides a kit comprising:
a bead-linked antibody that specifically binds to an epitope located in the sixth extracellular immunoglobulin-like domain of CD31 (e.g. PECAM 1.2); and
at least one fluorescently-labelled antibody that specifically binds to a protein selected from the group consisting of a CD31 protein comprising a phosphorylated tyrosine at position 686 (e.g. a labelled rabbit anti-CD31 phospho-tyrosine 686 polyclonal antibody, which may be labelled e.g. with AlexiaFluor®488-conjugated (Fab')$_2$ fragments); a CD31 protein comprising the sixth extracellular immunoglobulin-like domain (e.g. PECAM 1.2), a CD31 protein comprising the second extracellular immunoglobulin-like domain (e.g. WM59), CD3, CD28, SHP2, CD45, CTLA4, SLAM, p56LcK, CD3ζ, Zap70, NFkB, ERK, IkBK, RhoA, CsK and PTPase.

The invention also provides kits for analyzing other molecular complexes. Such kits may for example comprise a bead-linked antibody and at least one fluorescently-labelled antibody, wherein each antibody specifically binds to a protein selected from the group consisting of:
IgM, CD19, CD22, Iga/b ITAM, SYK, GRB2, BTK, PI3K, RAS, IKK, PKCb, RAC, SHP1, SHIP, PTEN and cleaved Notch;
IL-6R, Gp130, Jak1, Stat3, Gab, ERK, MAPK, SHP2, SOCS3;
Beta-integrin, Talin, Paxillin, Fyn, FAK, a-actinin, GRb2, Ras, Raf1, MEK1/2, ERK1/2, Sos and PTPase;
C83 (after shedding), b-secretase, a-secretase, C99 (left on by b-secretase) APP (on whole molecule), GSK3, Cdk5/p25, Cdk5/p35; or
FasL, FADD, TRADD, TNF-R1, RIP, Reaper, Caspases, FLIP, p53, Bax, BCL-2, Apaf-1, MDM2, c-Myc.

The kits according to the invention may further comprise a fluorescently-labelled antibody that specifically binds to phosphoTyrosins or to phosphoSerin/Threonins.

The different antibodies used in the methods and kits for analyzing a molecular complex do preferably not cross-compete with each other.

All references cited herein, including journal articles or abstracts, published or unpublished patent application, issued patents or any other references, are entirely incorporated by reference herein, including all data, tables, figures and text presented in the cited references.

Although having distinct meanings, the terms "comprising", "having", "containing' and "consisting of" have been used interchangeably throughout this specification and may be replaced with one another.

The invention will be further evaluated in view of the following examples and figures.

BRIEF DESCRIPTION OF THE FIGURES

FIG. 2 shows that the apparent loss of CD31 on lymphocytes is due to its extracellular shedding. a. Solubilized cell membrane-bound CD31 molecules were extracted from cultured Jurkat CD4+ T cells and coupled to fluorescent beads. The percentage of dom1-bead-bound molecules is <6% in resting conditions and >99% 5' after TCR engagement. b. Most soluble CD31 in culture supernatant (□) of TCR-activated T cells and in human plasma (▨) consists of a single truncated fragment comprising dom1-dom5 and lacking dom6. Negligible levels of truncated CD31 lacking both dom5 and dom6 could be detected only in plasma.

"VS" stands for the erythrocyte sedimentation rate. "CRP" stands for the C-reactive protein. "sCD31 Total" stands for the total level of soluble forms of CD31, measured with the method of the invention. "sCD31$^{clivé}$" stands for the shed extodomain of CD31, measured with the method of the invention.

Figure 6:
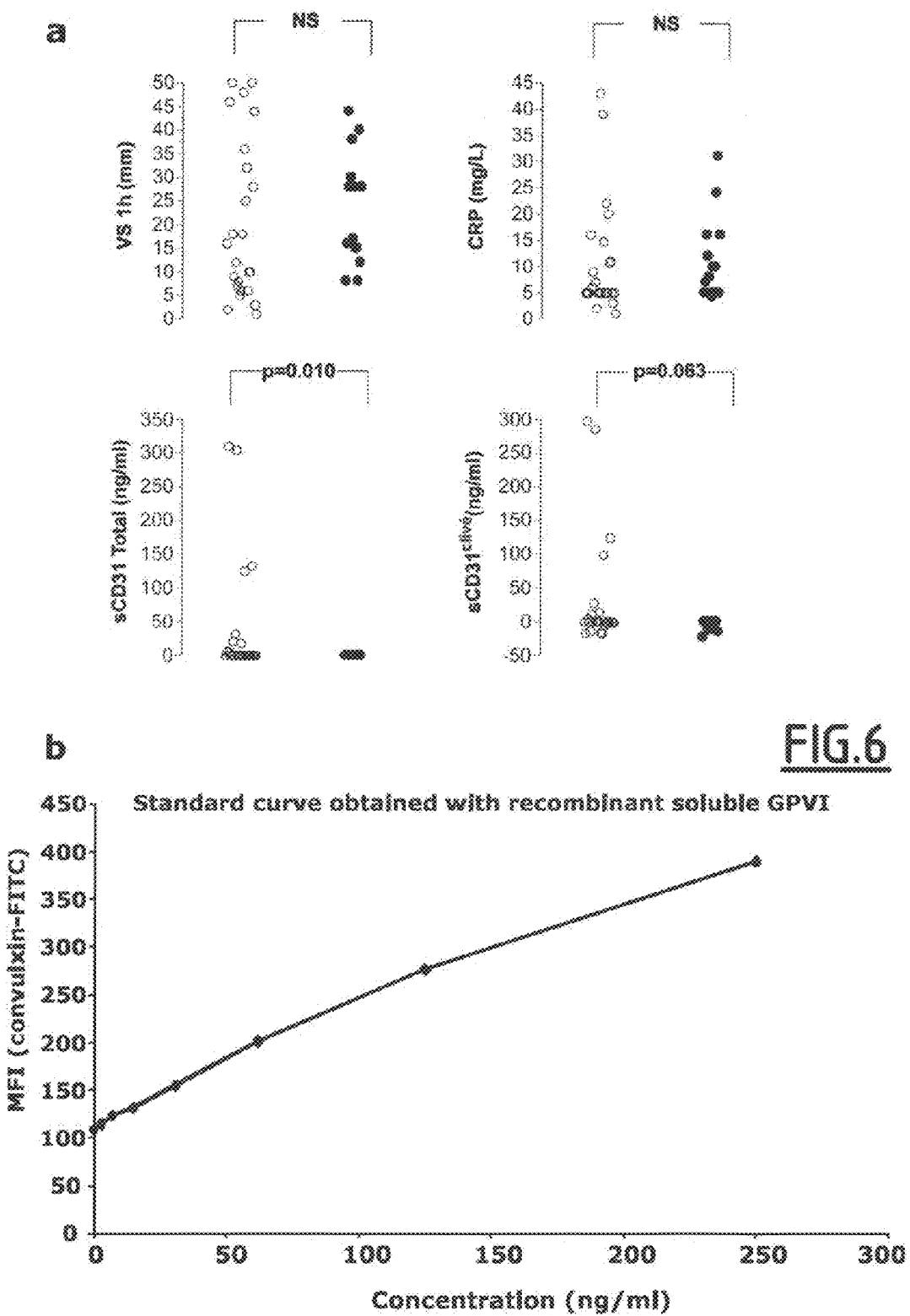
FIG. 6A shows that shed CD31 can be used as a diagnostic and/or prognostic marker for inflammatory diseases. White boxes are indicative of a bad prognostic of the patient, and black boxes are indicative of a good prognostic of the patient.

FIG. 6B shows that the method of the invention can be used for measuring shed ectodomains of GPVI.

BRIEF DESCRIPTION OF THE SEQUENCES

SEQ ID NO: 1 corresponds to the sequence of human CD31.

SEQ ID NOs: 2 and 3 correspond to CD31 peptides.

SEQ ID NO: 4 corresponds to a scramble peptide used as a negative control.

EXAMPLES

Example 1

Material and Methods

Assessment of CD31$^+$ and CD31$^{shed}$ blood leukocytes. Ten-color flow cytometry was performed on peripheral blood leukocytes from 5 healthy individuals either in basal conditions or after overnight stimulation with soluble 1 µg/ml of purified anti-CD3 antibody (R&D Systems). Ten-color flow cytometry was performed after erythrocyte hypotonic lysis (10 minutes at 37° C. 1:10 v:v in Tris 10 mM, NH$_4$Cl 155 mM, KHCO$_3$ 10 mM, pH 7.4) on heparinized peripheral blood leukocytes from 5 healthy individuals, fixed in PBS/Formaldehyde 1%/FCS 1% for 4 minutes at 37° C. prior to processing. All experiments on human blood were approved by the International Ethical committee (see world wide web page clinicaltrials.gov; Identifier: NCT00430820). Pelleted cells were incubated for 30 minutes at room temperature and protected from light with a cocktail of fluorescent monoclonal antibodies directed to CD3 (PE-Texas Red), CD4 (PE-Cy7), CD8 (PerCP), HLA-DR (APC-Cy7), CD45RA (Pacific Blue), and CD31 (WM59, PE) from BD Biosciences and anti-CD20 (AlexaFluor®700) and anti-CD31 (PECAM 1.2, FITC) from Invitrogen (1 µl of each). At least 50,000 events were acquired in the lymphocyte gate using a BD LSRII® equipped with 3 lasers (405, 488 and 633 nm) and analysed with BD DIVA® 6.0 software.

Subtractive measurement of soluble CD31. To detect the splice variant and truncated CD31 in plasma and the culture supernatant, a cytokine bead array (CBA®, BD) has been customized. Three differently functional CBA beads (A9, D5 and E9) were coupled with either one of the following purified monoclonal anti-CD31 antibodies JC70A (domain 1, DAKO), MEM-05 (domain 5, Zymed) and PECAM 1.2 (domain 6, Invitrogen). The coupled beads were then incubated with the plasma of the same 5 healthy controls or the culture supernatant and positive binding of circulating CD31 was detected by a fourth anti-CD31 monoclonal antibody, WM-59 (domains 1-2) coupled to PE (BD). The concentration of plasma CD31 including at least domain 1 (JC70A), or domains 1 to 5 (MEM-05) or all the extracellular domains 1 to 6 of CD31 (PECAM 1.2) was determined by analysing the median fluorescent intensity of the detecting antibody on 1000 gated beads on samples and serial dilutions of the same standard (recombinant, full length extracellular CD31, R&D Systems). The standard curve was obtained for each of the beads using the same known concentrations of the recombinant CD31 in order to overcome any bias due to differences in binding affinity of the diverse antibodies. The concentration in ng/ml of CD31 determined with PECAM 1.2 coupled beads (dom 1-6) was subtracted from the one obtained using MEM-05 coupled beads to obtain the amount of circulating CD31 lacking dom6 (dom 1-5). The latter was subtracted from the concentration of CD31 obtained using the JC70A-coupled beads to calculate the value of soluble CD31 lacking both dom 5 and 6 but containing at least domains 1 and 2 (dom 1-2).

Assessment of CD31-ITIM phosphorylation. Log-phase Jurkat cells ($10^7$ cells/condition) were either left unstimulated (negative control) or incubated with pervanadate (positive control) or stimulated with anti-CD3 and anti-CD28 antibodies (R&D Systems, 1 µg/ml each) in the presence or absence of peptide 551-574 (100 µM), or incubated with the peptide alone during 20 minutes. Cells were then lysed with 1 ml of RIPA buffer on ice for 30 minutes, ultracentrifuged and 16 µl of the supernatant was incubated with PECAM 1.2-coated Functional E9 CBA® beads (BD) for 2 hours at room temperature. Beads were subsequently washed with CBA washing buffer and incubated with 2 µl of undiluted rabbit anti-CD31 phospho-tyrosine 686 (pY686) sera followed by two washings and incubation with AlexaFluor®488-conjugated (Fab')$_2$ fragments (1:100 in CBA washing buffer) of goat-anti-rabbit IgG (Invitrogen). The beads (2000/condition) were finally analysed by flow cytometry in the FITC channel (530/30 nm) and data are expressed as Median fluorescence intensity (MFI)±the percentage of the coefficient of variability (% CV) calculated with the DIVA 6.0® software (BD). Duplicate lysate aliquots and serial dilutions of recombinant CD31 were incubated with the PECAM 1.2-coated beads and the amount of dom1+ cell-bound CD31 was revealed using anti-CD31 VM59-R-PE (dom1) and PECAM 1.2-FITC (dom6) antibodies.

Fluorescent peptide binding. For visualisation of peptide binding to $CD31^+$ and $CD31^{shed}$ $CD4^+$ T cells, freshly purified peripheral blood leukocytes prepared as above were washed with a buffered solution containing 2 mM EDTA (to avoid endocytosis of the peptide) and incubated overnight at room temperature in a dark humidified chamber with 50 µM FITC-labelled CD31 peptide 551-574 and 1:10 dilution of fluorescent monoclonal anti-CD31 (PE) and anti-CD4 (APC) antibodies (BD Biosciences) in a poly-D-Lysine coated Ibidi® 8-well culture chamber (Biovalley). Cells were then washed twice, nuclei counterstained with DAPI and digital images of a 0.3 µm intracellular section were acquired on a Zeiss Axiovert M200 microscope (×63 immersion objective) equipped with the ApoTome® and a cooled monochromatic digital camera (Zeiss).

Calcium mobilization assay. Spleen cells from C57Bl/6 mice were prepared as described in Caligiuri et al. (2005 Arterioscler Thromb Vasc Biot 25:1659-1664). Cells were incubated with Fluo-3AM (Invitrogen, # F1242) as per the instructions of the manufacturer. Fluorescence of calcium-bound tracer was measured in the FITC channel on an LSRII® cytometer (BD Biosciences) prior to and during 60 seconds following the addition of hamster anti-mouse CD3/CD28 monoclonal antibodies (40 µg/ml each) and rat/hamster compBead® (1:50) either alone or in the presence of rat anti-mouse CD31 antibody (clone 390, 10 µg/ml) or in the presence of CD31 peptide 551-574 (100 µM). Negative controls included rat IgG isotype control and scramble peptide. Antibodies and compBeads® were from BD Biosciences.

Plasmon Surface Resonance. Homophilic binding association and dissociation constants were calculated by surface plasmon resonance (BIAcore® 2000, GE). In brief, peptide 551-574 was coated at 3400 resonance units (RU) on CM5 chips according to the manufacturer's instructions. Soluble peptide 551-574 (12.5, 25, 50 and 100 µM in 200 µl of 10 mM HEPES pH 7.4, 150 mM NaCl, 0.005% Tween 20) was injected at 20 µl/min at 25° C., on the peptide-coated channel and on an uncoated channel. Dissociation was monitored for 300 seconds. Association (kon) and dissociation (koff) constants were calculated using the BIAevaluation® 3.0 Software (GE). Injection of peptide 551-574 on a channel coated with the scramble peptide yielded negligible signal.

Evaluation of immunoregulation in vitro. $CD8^+$ T cell-mediated cytolytic activity against allogeneic mouse aortic smooth muscle cells and measurement of macrophage gelatinase (MMP-2/9) activity were performed as previously described for human cells in Caligiuri et al. (2006 Arterioscler Thromb Vasc Biol 26:618-623) using kits and reagents from Invitrogen. Briefly, primary cultures of FVB/N mouse aorta smooth muscle cells were labelled with the lipophylic tracer DIO (green) and co-cultured for 3 hours with CD8+ T cell-enriched spleen cells from C57Bl/6 mice (n=3 scramble peptide and n=3 peptide 551-574, 50 µM). Cytolysis was evaluated by intracellular accumulation of propidium iodide (PI). Cells were analysed by flow cytometry and the % of cytolysis was calculated by expressing the number of dead (PI+) cells among the target (DIO+) cells. Intracellular MMP-2/9 (gelatinase) activity was measured by flow cytometry in 7-day bone-marrow derived macrophages from C57Bl/6 mice (n=3 scramble peptide and n=3 peptide 551-574, 50 µM) three hours after the incorporation of OregonGreen® gelatine (MFI). T-cell proliferation was performed using either human peripheral blood mononuclear cells of spleen cells from C57Bl/6 ($CD31^{+/+}$) and $CD31^{-/-}$ mice (Charles River France) as previously described (Caligiuri et al. Arterioscler Thromb Vasc Biol 25:1659-1664). Briefly, cells were plated in triplicates at $0.2 \times 10^6$ cells/well in a U bottom 96-well plate in complete medium (RPMI 1640, 1% pyruvate, 1% glutamine, 1% penicillin-streptomicyne-fungizone, 10% decomplemented fetal calf serum, all from Invitrogen) containing 1 µg/ml anti-mouse CD3/CD28 or 5 µg/ml anti-human CD3 antibodies (BD) as appropriate. CD31 (551-574) and scramble peptide at 25, 50 and 100 µM final concentration were deposited in the wells just before cell plating. Plated cells were cultured for 72 hours in 5% $CO_2$ at 37° C. ($^3$H) thymidine (0.5 µCi/well) was added for the last 16 hours and proliferation evaluated using a Tomtec harvester and analysis on a Wallac micro beta counter. Data are expressed as mean±SEM of cpm in triplicates.

Evaluation of immunoregulation in vivo. Delayed type hypersensitivity (DTH) suppression was evaluated as described in the "Current Protocols in Immunology (2001) 4.0.1-4.0.2 Unit 4.2". Briefly, TNCB (2-chloro-1,3,5-trinitrobenzene, Fluka #79874) was dissolved in acetone/olive oil (1:1 v/v) at a concentration of 10 mg/ml. BALB/c mice (n=6/group) were primed by painting the shaved regions of the abdomen a with a total 0.2 ml of the preparation (n=6/group). The experiment included 3 groups for peptide 551-574 (10, 50, 100 µM) and 1 group treated with scramble peptide at 100 µM). Five days after priming, 10 µl of the TNCB-solvent mixture was painted on the right pinna, 30 minutes after subcutaneous (interscapolar) administration of the peptide 551-574 or the scramble peptide. Ear thickness increases were calculated by subtracting the thickness of the right and the left pinna of each mouse (right-left/left×100), measured at 24 h with a dial caliper ("Pocotest", Kroeplin Langenmesstechnick). The measure was performed 5 times on each ear and averaged for further analysis. The immunosuppressive effect of the peptide was calculated as % suppression= $(1-\Delta TE/\Delta TS) \times 100$, where $\Delta T$=(ear thickness 24 hr after elicitation)−(baseline ear thickness), E=sensitised animals, S=treated animals. Data are expressed as mean±SEM.

Detection of atherosclerotic lesion size and aneurysm formation. Male 28-week old apolipoprotein $E^{-/-}$ mice (n=8-10 mice/group) from our breeding facility were maintained on a regular chow diet and kept under standard conditions. Acceleration of atherosclerosis and aneurysm formation was induced by subcutaneous angiotensin II (Sigma, #A9525) infusion (1 mg/kg/d) for 28 days using osmotic minipumps (Alzet, #2004) as previously described (Daugherty et al. J Clin Invest 105:1605-1612). All experiments were approved by our institutional Ethical committee. Atherosclerotic lesions size were measured as previously described (Caligiuri et al. Arterioscler Thromb Vasc Biol 25:1659-1664). These experiments were repeated twice with similar results.

Peptides. All experiments on human material were carried out using the human peptide sequence while the mouse equivalent was used in all mouse experiments. The sequences of the peptides are shown in the table below.

```
                                        SEQ ID NO: 2
Human     NH2 - NHASSVPRSKILTVRVILAPWKK - COOH SEQ ID NO: 3
Mouse     NH2 - SSMRTSPRSSTLAVRVFLAPWKK - COOH SEQ ID NO: 4
Scramble  NH2 - SMPAVRSRFSATSLVTLKSRWPK - COOH
```

Example 2

Figure 1:
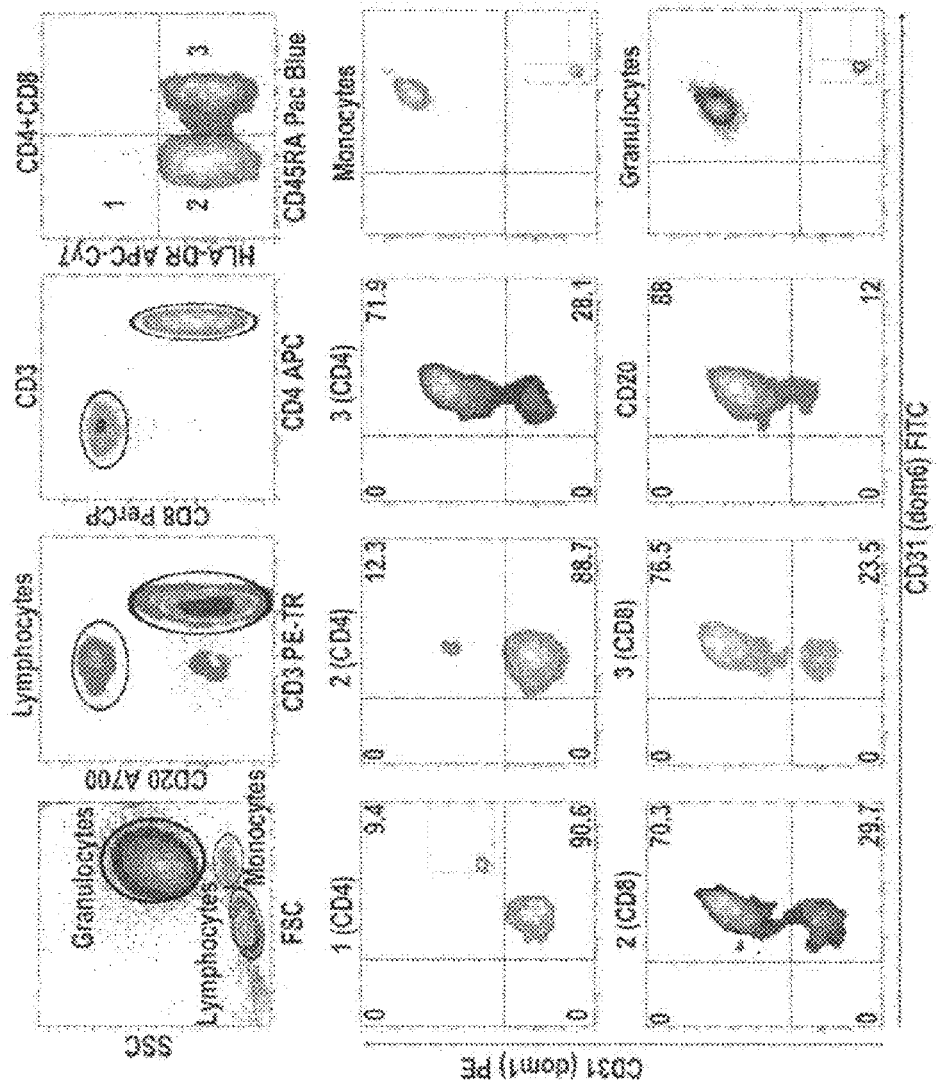
FIG. 1 shows a representative example of 10-color flow-cytometry analysis of human peripheral blood cells from a healthy donor. Isotype controls of antibodies anti-CD31 dom1 and anti-CD31 dom6 are shown in the insets. Lymphocytes, Monocytes and Granulocytes were gated within the FSC/SSC scatter. B (CD20 A700+) and T (CD3 PE-TR+) lymphocytes were identified and gated within the "Lymphocytes" and CD8+ (PerCP) and CD4+ (APC) subpopulations were gated within T lymphocytes. CD8+ and CD4+ T cells were further analyzed for the expression of HLA-DR and CD45RA and accordingly subdivided in activated (1), memory (2) and naïve (3) cells. All leukocytes were positive for CD31 dom6. Lack of dom1 increased from naïve (3) to memory (2) to activated (1) T cells.

The Apparent Loss of CD31 at the Surface of Blood Lymphocytes is Due to its Shedding Between the 5th and 6th Extracellular Ig-Like Domains In order to establish whether the loss CD31 was restricted to part or extended to the totality of its 6 extracellular Ig-like domains, a multicolor flow cytometry analysis of whole blood leukocytes from 5 healthy donors using two different antibodies specifically recognizing the membrane-distal and membrane-proximal Ig-like domains of the molecule was performed. To be able to discriminate between the different leukocyte populations and assess their state of maturation and activation, a panel of lineage markers as well as the expression of CD45RA and HLA-DR were simultaneously used. While the expression of CD31, as detected by a monoclonal antibody specific for the first domains of CD31 (clone WM-59, dom1-2) was recognized on naïve but not on activated/memory blood T cells, all cells expressed the membrane-proximal extracellular fragment of the molecule detected by another monoclonal antibody specific for the $6^{th}$ Ig-like domain of CD31 (clone PECAM 1.2, dom6), irrespective of their state of maturation/activation (FIG. 1).

Flow cell cytometry showed that T-cell receptor (TCR) engagement induces a shift of >80% of blood resting T cells from a CD31 dom1$^+$/dom6$^+$ to a dom1$^-$/dom6$^+$ (CD31$^{Shed}$) phenotype. Molecular analysis of the membrane proteins from cultured T-cell lysates demonstrated that >99% of the T cell-bound CD31 molecules drop the distal portion containing dom1 already 5' minutes after TCR stimulation in vitro (FIG. 2a). Analysis of the supernatant showed that, simultaneously, a single truncated soluble protein limited to the first 5 Ig-like domains of CD31, accumulates in the culture supernatant (FIG. 2b). Furthermore, the analysis of the plasma of the same healthy donors showed that major part of soluble CD31 in plasma was constituted of a truncated molecule comprising Ig-like domains 1 to 5 and specifically lacking the membrane-proximal $6^{th}$ domain (FIG. 2b) that always remains anchored to the apparently CD31-negative (CD31 dom1$^-$) lymphocytes both in vitro and in vivo. Only a minimal fraction of soluble CD31 contained all 6 extracellular domains predicted in the previously reported (Goldberger et al. J Biol Chem 269:17183-17191) variant spliced form both in culture supernatant and in plasma (FIG. 2b). No significant other cleavage of the molecule occurs upstream of the $5^{th}$ domain since the latter was virtually always present concomitantly with the first domain in the truncated soluble CD31 proteins (FIG. 2b).

Here it is demonstrated that the assumed loss of the molecule on activated/memory T lymphocytes is actually incomplete and results from shedding of CD31 between the 5th and 6th extracellular Ig-like domains. CD31 shedding occurred immediately after cell activation on T lymphocytes and was accompanied by the accumulation of the truncated molecule in the supernatant together with trace levels of the spliced variant produced by the cells. This finding was unsuspected because all commercially available tests to detect plasma CD31 use antibodies directed to CD31 domains 1 to 5, and therefore cannot discriminate between the spliced variant (containing all the 6 extracellular domains) and the truncated (domains 1 to 5) forms of CD31. The subtractive immunosorbent assay described herein is able to discriminate between the two forms of soluble CD31 and precisely quantify the proportion of each of them in the plasma. This assay showed that the major part of plasma CD31 comprises domains 1 to 5 but lacks the membrane-proximal 6th domain, which remains anchored to blood CD31 dom1-lymphocytes. Therefore, it is proposed to refer to these lymphocytes as CD31 shed rather that CD31 "negative" cells. Previous work in vitro had indicated that CD31 shedding at an unidentified position N-terminal from the transmembrane segment of the molecule can occur in endothelial cells undergoing apoptosis (Ilan et al. 2001. Faseb J 15:362-372). For the first time, it is shown herein that shedding is responsible for the CD31 (incomplete) loss on blood lymphocytes and that the circulating CD31 consists mainly of a truncated form derived from its cleavage between the Ig-like domains 5 and 6, rather than of the secreted spliced variant form. Genetic polymorphisms for CD31 have been described, but the predictive value of soluble CD31 levels was conflicting either in atherothrombosis or other dysimmune diseases. In fact, while the amount of the spliced form can be predicted by different genetic variants, the proportion of the form resulting from protein shedding is not determined by CD31 gene polymorphism. It is proposed that the disparity between the different studies was due to fact that circulating CD31 is a mixture of the genetic variant and of the truncated form and discrimination between the two forms of CD31 was not possible. The subtractive method described herein will allow the differentiation of the prognostic value determined by genetic variants of CD31 independently of that linked to CD31 shedding.

Example 3

Figure 3:
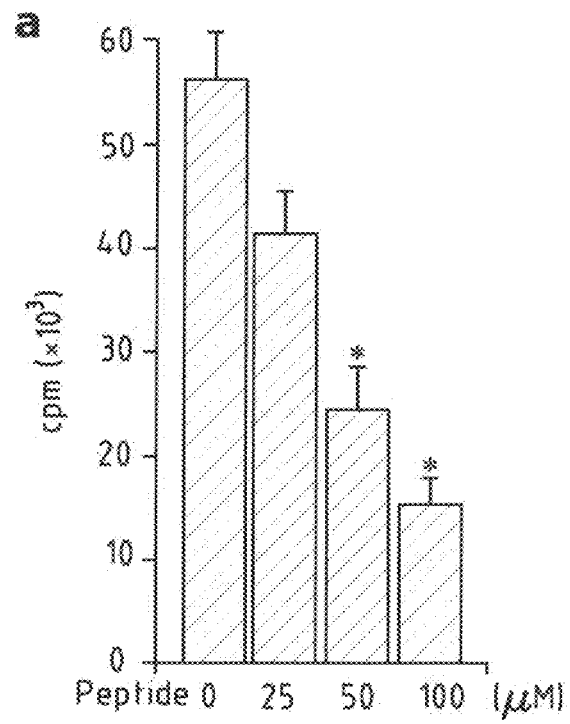
FIG. 3 shows that a peptide homotypic of the residual extracellular fragment on CD31$^{shed}$T induces CD31-ITIM phosphorylation. a. Proliferative response to TCR engagement of human peripheral blood mononuclear cells in the presence of increasing doses of CD31 peptide 551-574. *$p<0.05$ vs dose "0". b. Flow cytometry assessment of 686ITIM phosphorylation on solubilized membrane-bound CD31 from cultured Jurkat CD4+ T cells. Solubilized proteins were captured by E9-PECAM-1.2 (dom6) functional CBA beads and detection was carried out by anti-pY686 rabbit sera followed by AlexaFluor®488-anti-rabbit secondary antibody. The histogram shows the Median Fluorescent Intensity (MFI)±the % of the variability coefficient (CV %) of Alexafluor®488 (pY686) over 2000 E9-PECAM 1.2 acquired beads. Pervan=positive control (pervanadate); CD3/CD28=anti-CD3 and anti-CD28 antibodies (1 µg/ml each); peptide=CD31 peptide 551-574 (100 µM).
Figure 3:
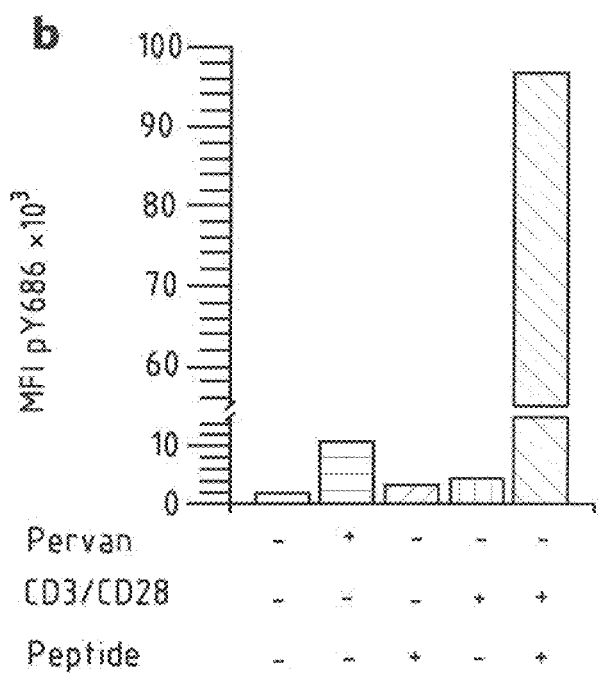
Figure 4:
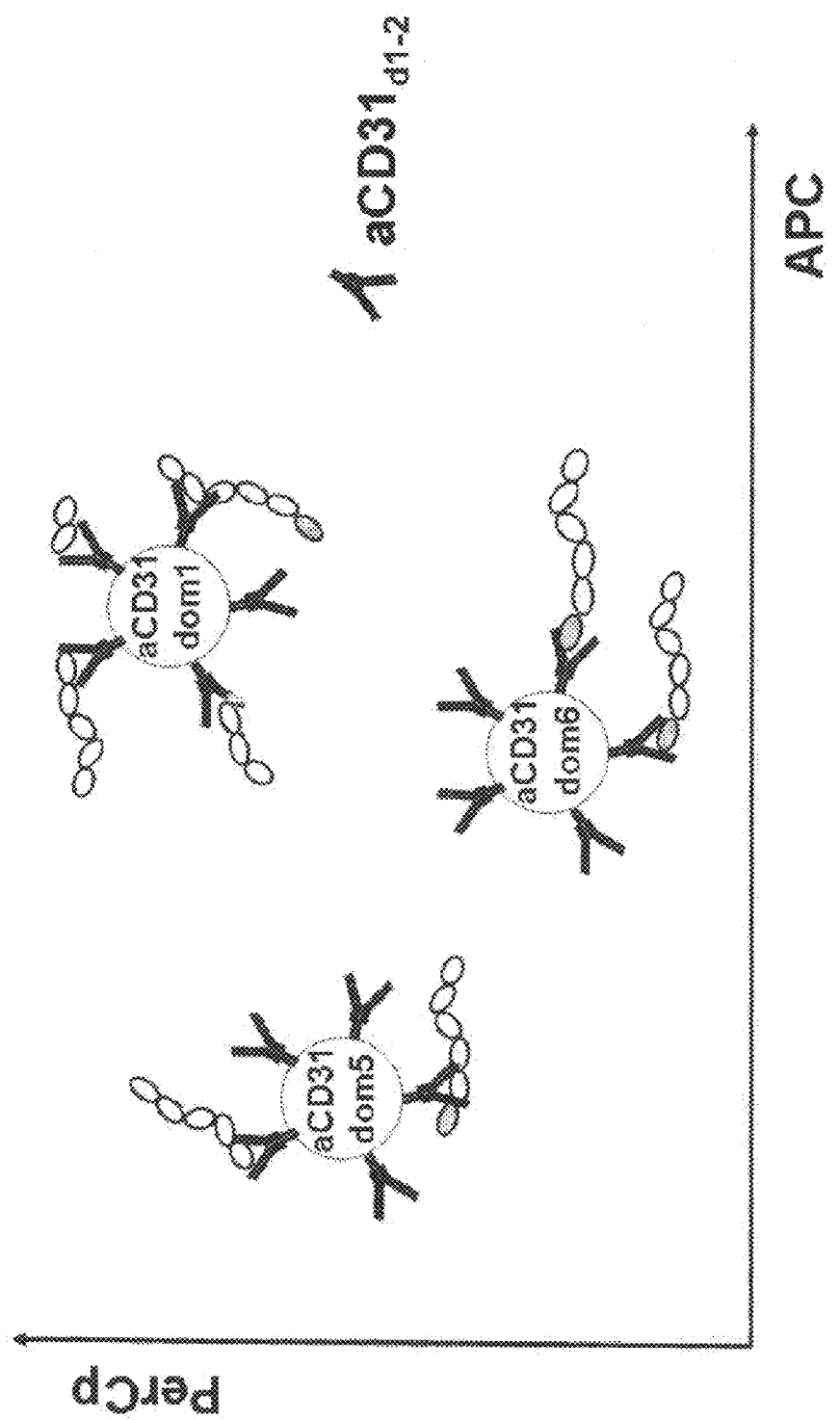
FIGS. 4 and 5 illustrate the principle of the method of according to the invention. On FIG. 5, the black box represents a discriminating antibody. The white box represents a capture or a signaling antibody.
Figure 5:
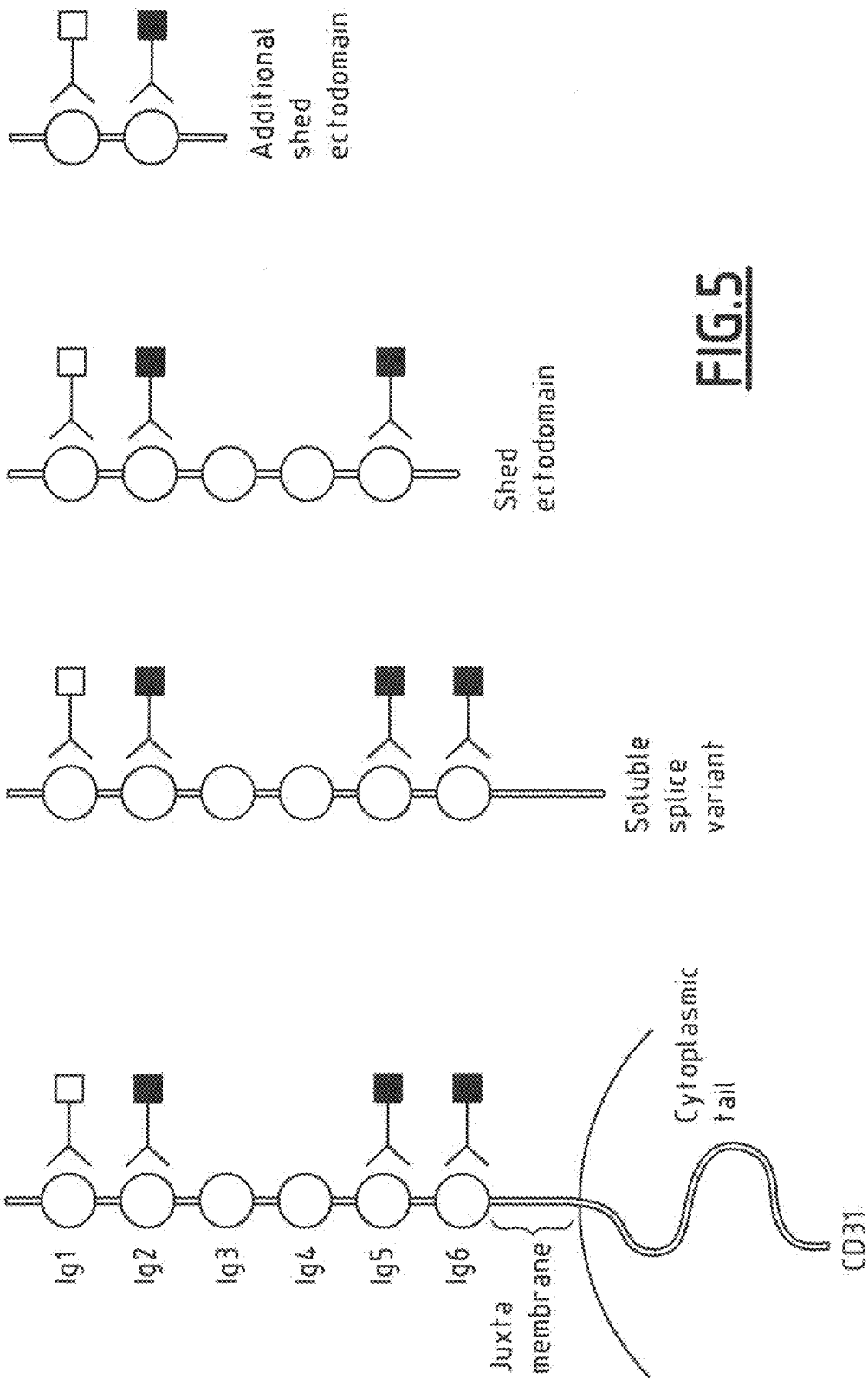

A Peptide Contained in the Residual Extracellular CD31 Fragment on CD31$^{shed}$ T Cells Enhances Phosphorylation of CD31-ITIM A CD31 dom6-derived synthetic peptide corresponding to the juxta-membrane 23 aminoacids (551-574) of the ectodomain of the human molecule binds both to CD31 dom1$^+$ and to CD31 dom1$^-$ (CD31$^{shed}$) CD4$^+$ T lymphocytes ex vivo. Importantly, the binding of this peptide on T cells has functional consequences on immune cell control since it exerted dose-dependent inhibition of human peripheral blood T-cell proliferation in vitro (FIG. 3a). To assess whether the inhibitory effect of the peptide could be mediated by homophilic binding and engagement of the CD31 signaling, the level of phosphorylation of the CD31 ITIM tyrosine at position 686 ($_{686}$ITIM) in cultured T cells was evaluated. Stimulation of the TCR by anti-CD3 and anti-CD28 antibodies alone or the sole presence of the peptide induced a minor increase of CD31 pY686 (FIG. 3b) but concomitant TCR-stimulation in the presence of the peptide boosted the phosphorylation the CD31$_{686}$TIM by a factor of >23 (FIG. 3b).

Example 4

Detection of Shed Cd31 in Plasma from Patients Suffering from Atherothrombosis and in Unaffected Individuals The total amount of CD31, the amount of shed CD31 and the amount of spliced CD31 has been measured both in eleven individuals suffering from atherothrombosis and in twenty-three unaffected individuals.

The group "Atherothrombosis" comprised eleven individuals suffering from chest pain even at rest and presenting an abnormal coronarography.

The group "No Atherothrombosis" comprised twenty-three individuals. A sub-analysis was carried out on the group "No Atherothrombosis", which was found to comprise:

eight individuals presenting a normal coronarography and a normal carotid echodoppler in spite of chest pain;

four individuals presenting a normal coronarography in spite of chest pain, but in whom atherosclerosis was detected by carotid echodoppler; and eleven individuals suffering from chest pain only on effort and presenting an abnormal coronarography (i.e. suffering from coronary atherosclerosis without thrombosis).

The total amount of CD31, the amount of shed CD31 and the amount of spliced CD31 was determined as follows.

1. The total amount (1 µl/test) of beads (E9, coupled with clone JC70A, DAKO) was transferred to a conical tube and centrifuged at 200 g for 5 minutes. The supernatant was carefully discarded and replaced with same amount of serum enhancement buffer (BD #51-9002150), and incubated at room temperature for 15 minutes.

2. The fluorescently-labeled antibody mix (PE-WM59; FITC-HC1/6; PB-PECAM1.2) was prepared, each at 1 µg/ml, 1 µl each/condition.

3. 1 tube precondition was prepared, each containing 3 µl of a standard dilution or a plasma sample. The reconstituted beads were centrifuged at 200 g for 5 minutes, the supernatant was discarded and the serum enhancement buffer was replaced with the fluorescently-labeled antibody mix. 3 µl of this solution was distributed in each of the tubes containing the standard dilution and samples, and the solution incubated for 1 hour at 4° C. in the dark.

4. 150 µl of Washing buffer (BD # 51-9003797) were added to each tube, and the signal was acquired.

As shown in the table below, the percentage of shed CD31 was higher in individuals suffering from atherothrombosis than in unaffected individuals, in spite of the fact that all individuals were suffering from chest pain.

| CD31 Plasma Level (ng/ml) | total | splice | shed |
|---|---|---|---|
| Atherothrombosis (n = 11) | 11.55 ± 0.7 | −7.02 ± 2.69 | 18.57 ± 2.67 |
| No Atherothrombosis (N = 23) | 11.58 ± 0.49 | 5.26 ± 1.850 | 6.31 ± 1.85 |
| T-test Prob > F | 0.9756 | 0.0007 | 0.0006 |

Total CD31 amounts were similar in the four groups, while the amount of shed CD31 and the amount of spliced CD31 were significantly different in each paired group comparison. Shed CD31 was increased in individuals with abnormal coronarography, with highest values in those suffering from atherothrombosis. Splice CD31 was still present in patients suffering from atherosclerosis without atherothrombosis, while it was almost undetectable in patients suffering from atherothrombosis.

These results demonstrate that high levels of CD31 soluble splice variants associated with low levels of shed CD31 indicates that the patient suffers from non specific chest pain, eventually associated with carotid plaques. A slight increase of shed CD31 levels associated with normal or reduced levels of CD31 soluble splice variants indicates that the patient suffers from atherosclerosis. An important increase of shed CD31 levels associated with undetectable amounts of CD31 soluble splice variants indicates that the patient suffers from atherothrombosis.

Example 5

Use of CBA® Beads for Quantitative Assessment of Protein Association and of Phosphorylation 8.1. Protocol Used for Assessing the CD31 ITIM-Dependent Inhibitory Pathway in T Cells Lysis of the cells. Jurkat T cells in log phase (10×10$^6$/ml, 1 ml) were either left untouched (negative control) or incubated with Na$_3$VO$_4$/H$_2$O$_2$ (sodium ortovanadate which is a tyrosin phosphatase inhibitor, positive control for tyrosin phosphorylation). In parallel, cells were stimulated either with CD3 or with CD3+ CD31 (domain 2, WM-59 antibody) by antibody-mediated crosslinking. After 20' incubation at 37° C. in 5% CO$_2$, the cells were lysed on ice for 30' with a RIPA buffer containing a cocktail of protease and phosphatase inhibitors. Lysates were ultragentrifuged and supernatants were used either straightforward or aliquoted and stored at −20° for further analysis.

Capture of the target protein on a solid support (1 hour at room temperature). This step follows the principle of immunoprecipitation but the signaling complex is nor denatured neither reduced, and no electrophoresis and/or blotting is carried out. As a solid support, CBA® functional beads previously coupled with an antibody directed to the membrane-proximal CD31 Ig-like domain 6 (clone MBC 78.2 also called PECAM1.2) were used following the manufacturer's instructions. An aliquot of 20 µl of lysate supernatant from each condition was incubated with 5 µl PECAM1.2-CBA® for 1 hour at room temperature.

Detection of molecules associated with CD31 and of the phosphorylation state of CD31 ITIM 686. After washing of the beads once with CBA washing buffer (100 µl/tube), the beads were been aliquoted in 4 separate tubes and incubated with fluorescent antibodies directed to:

CD3-FITC;
CD28-PE;
CD31 domain 6 (PECAM1.2 FITC)
CD31 domain 2 (WM-59 PE)

phosphoTyrosin (clone 4G10 FITC);
phosphoSerin/Threonin (labelled with FITC)
CD31 phosphotyrosin 686 (rabbit polyclonal conjugated with alexafluor 488 antirabbit secondary antibody); or
SHP2-PE.

After 1 hour incubation at room temperature in the dark, beads were washed once with 100 µl CBA washing buffer and more than 600 beads were acquired using an LSR II and DIVA® software.

4. Analysis. The median fluorescence in each fluorescent channel was recorded. The DIVA® software also calculated the % CV (variability coefficient), which can be considered as an equivalent of error bar value for repeated measure and allow statistical comparison between samples.

8.2. Results

The results are shown in the tables below.

|  |  | (ng/ml) CD31 dom6 | (ng/ml) CD31 dom2 | % shed CD31 | MFI pY (4G10) | MFI pSer/ pThreo |
|---|---|---|---|---|---|---|
| Negative control | unstimulated | 19 | 18 | 5 | 485 | 284 |
| Positive pY control | Na3VO4/H2O2 | 103 | 77 | 25 | 1205 | 324 |
| T-cell activation | CD3 crosslink | 9080 | 83 | 99 | 2681 | 130 |
| Antibody CD31 treatment | CD3 + CD31 crosslink | *2389* | *46* | *98* | *2312* | 267 |
| Peptide CD31 treatment | CD3 crosslink + CD31 peptide | 10962[1] | *67*[2] | 99 | 3277[3] | 329 |

|  | MFI CD31 pY686 | MFI SHP-2 | MFI CD3 | MFI CD28 |
|---|---|---|---|---|
| Negative control | 1578 | 165 | 197 | 8165 |
| Positive pY control | 10667 | 193 | 354 | 3932 |
| T-cell activation | 4198 | 90 | 17876 | 25169 |
| Antibody CD31 treatment | *2268* | 149 | *2425* | *17147* |
| Peptide CD31 treatment | 96632[3] | 185[4] | *20096*[5] | *24306*[5] |

A value in bold indicates an increase versus CD3 crosslink conditions, and values in italic indicate a decrease.

[1] Engaged CD31 molecules oligomerize in cis. CD31 molecule being physiologically engaged as a regulatory molecule in T-cell activation, this explains the increase of CD31 domain 6 amount in T-cell stimulated samples.

[2] If only domain 2 of CD31 was detected, one would conclude that the amount of the captured molecule was similar in all samples. Indeed, most of CD31 cis-oligomerized molecules are shed between domain 6 and 2 upon T-cell activation as show in the column "% shed".

[3] Total phosphoTyrosin is slightly decreased by CD31 antibody treatment while it is slightly increased by CD31 peptide treatment. Indeed, not only CD31 ITIMs can be phosphorylated, but also tyrosins present on other membrane proteins (e.g. CD3 and CD28) which are associated with CD31 upon T-cell activation. The differences specific for CD31 phosphoITIMs could detected by using antibodies directed to sequence-specific phosphoITIM. Not only phosphotyrosine are increased, but also phosphoserine/threonine. These aminoacid can be phosphorylated either in the CD31 cytoplasmic tail, or in one of the associated molecule.

[4] The amount of SHP-2 associated to CD31 is increased by 50% with the antibody treatment and by 100% with the peptide treatment.

[5] The amount of activating receptor (CD3) and the costimulatory molecule associated to the CD31 (CD28) are decreased by the antibody treatment, while they are increased by the CD31 peptide. This can be viewed as a counter-regulatory mechanism of the cell in the view of the dramatic increase of CD31 ITIM phosphorylation that counteracts T-cell activation.

8.3. Conclusion

All these data were acquired starting from a very small amount of the same sample (20 µl). The use of multicolor flow-cytometry warrants their analysis in a simultaneous way. The availability of a standard allows exact determination of absolute amounts of each molecule in the signaling complex.

The above experiment was performed using either FITC (FL1) or PE (FL2) conjugated antibodies. The use of non-fluorescent beads for protein capture allows the use of at least two other fluorophores for use in the blue laser (PerCP or PE-Cy7 or PE-Cy5, FL3 and APC or Cy5, FL4). The availability of additional lasers (red, violet, uv) on the cytometer further expands the capacity of this method. Up to 17 different fluorescent antibodies can be used simultaneously and therefore up to 17 different parameters (associated membrane protein, signaling molecules, phosphorylated sequences) can be detected simultaneously on the same sample, with a powerful statistical value due to the high number of beads that can be acquired.

The above method has numerous advantages compared to prior art methods. The table below compares this method with co-IP/WB, CBAFlex and CASE/Phosphlow.

| Operation | IP/WB | CBAFlex | Phoflow/ CASE | Method according to the invention |
|---|---|---|---|---|
| Protein extraction | 30 min | 30 min | N/A | 30 min |
| Immunoprecipitation | 1-12 h | N/A | N/A | N/A |
| SDS-PAGE | 2 h | N/A | N/A | N/A |
| Blot | 2 h | N/A | N/A | N/A |
| Fixation | N/A | N/A | 1 h | N/A |
| Blocking | 1 h | N/A | 1 h | N/A |
| Primary Antibody | 1-18 h | 1 h | 1 h | 1 h |
| Washing | 30 min | 5 min | 15 min | 0-5 min |
| Secondary Antibody | 1 h | N/A | 1 h | N/A |
| Washing | 30 min | N/A | 15 min | N/A |
| Detection develop. | 60 min | N/A | 15 min | N/A |
| Data Acquisition | 1 h | <10 sec/samp | 15 min | <10 sec/samp |
| Multi-target | N/A | up to 20 | ≥2 | up to 20 |
| Time | ~12-36 h | ~1.5 h | ~7 h | ~1.5 h |

-continued

| Operation | IP/WB | CBAFlex | Phoflow/CASE | Method according to the invention |
|---|---|---|---|---|
| Sample size | ≥100 μL | 20-50 μl | ≥50 μL | ≤5 μl |
| Specific interactions | Yes (1) | N/A | N/A | Yes (≥1) |

Compared to co-IP/WP, this method is quantitative, direct and much more rapid. In addition, it allows the simultaneous detection of the target protein, of phosphomolecules and of associated membrane and intracellular molecules. It also allows the simultaneous analysis of much more parameters since a Western Blot can only be rehybridized a limited number of times, whereas up to 20 antibodies can be used simultaneously in the frame of this method with the most recent generation of cytometers.

Compared to CASE/Phosphlow, or CBA Flex set, this method is much more specific since the target molecule is captured and the interactions within the molecular complex can be analyzed. In addition, it allows the simultaneous detection of the target protein, of phosphomolecules and of associated membrane and intracellular molecules.

Example 6

Optimization of the Protocol

5 μl of sample are incubated for 30-60' at 4° C. in the dark with 1 μl of a mix containing functional CBA beads-immobilized monoclonal MEM-05 antibody (CD31 domain 5, Exbio, Caltag), WM-59 (CD31 domain 2) and PECAM 1.2 (also called MBC 78.2, CD31 domain 6) coupled to a fluorophore. After incubation, beads are diluted with 200 μl of assay diluent buffer and acquired. The median fluorescent intensity of the PE and FITC channel on more than 1000 gated beads is analyzed on samples and serial dilutions of the standard (recombinant, full length extracellular CD31, R&D Systems). Two standard curves are obtained with each of the detecting antibodies simultaneously used with recombinant CD31 in order to overcome any bias due to differences in binding affinity of the diverse antibodies. With three discriminating antibodies directed to domains 2, 5 and 6, it is possible to discriminate full CD31 from CD31 lacking either domain 6 (Δ6) from CD31 lacking both domain 5 and 6 (Δ5-6).

To increase the specificity of the test, monoclonal antibodies directed to CD31 domain 1 (clone JC70A, Dako) are coupled to capture beads. Detection is based on three fluorescent antibodies directed to CD31 domain 2 (WM-59, BD), domain 5 (HC1/6, Biosource) and domain 6. Purified PECAM 1.2/MBC 78.2 is coupled with a suitable fluorophore. With current functional beads, an optimal set of fluorophores is FITC, PE and PerCP. This combination allows measurement on any basic blue-laser cytometer (FACScan, FACSCalibur, etc) available in hospital biology laboratory.

With FITC and PE as fluorophores (see example 5), the lowest detection limit is 3 ng/ml. This results in negative values of spliced CD31 in patients presenting a high risk of suffering from atherothrombosis. In contrast to this, different fluorophores may lead to an increased sensitivity. Therefore, different combinations of fluorophores and of antibodies are tested.

Example 7

Analysis of the BIOcore Cohort

A cohort of patient has been analyzed. The individuals were classified in different groups, as set forth in Example 4.

The cell analysis by cytometry confirmed that the percentage of T (CD3+) lymphocytes that display a truncated (shed) CD31 is significantly higher in patients at risk of acute coronary events (see Table 1).

TABLE 1

Oneway analysis of CD31shed (% of CD3 cells) by Group

| Level | - Level | Difference | Lower CL | Upper CL | p-Value |
|---|---|---|---|---|---|
| ACS | Norm | 16.06119 | 10.7395 | 21.38292 | <0.0001* |
| ACS | Carotide | 15.99231 | 9.6004 | 22.38419 | <0.0001* |
| ACS | SA | 12.79007 | 7.9876 | 17.59257 | <0.0001* |
| SA | Norm | 3.27111 | −2.2928 | 8.83498 | 0.2462 |
| SA | Carotide | 3.20223 | −3.3926 | 9.797.9 | 0.3377 |
| Carotide | Norm | 0.06888 | −6.9132 | 7.05092 | 0.9844 |

In the above table, "ACS" stands for acute coronary syndromes, "Carotide" stands for peripheral atherosclerosis, "Norm" stands for normal coronary angiogram, and "SA" stands for stable angina.

Subpopulation analysis showed that this conclusion is valid both for CD4+ T (CD3+) cells and for CD8+ T (CD3+) cells (see Tables 2 and 3, respectively).

TABLE 2

Oneway analysis of CD31shed (% of CD4 cells) by Group

| Level | - Level | Difference | Lower CL | Upper CL | p-Value |
|---|---|---|---|---|---|
| ACS | Carotide | 26.37179 | 18.2050 | 34.53856 | <0.0001* |
| ACS | Norm | 19.24452 | 12.4451 | 26.04397 | <0.0001* |
| ACS | SA | 16.43631 | 10.3003 | 22.57235 | <0.0001* |
| SA | Carotide | 9.93548 | 1.5094 | 18.36157 | 0.0213* |
| Norm | Carotide | 7.12727 | −1.7935 | 16.04806 | 0.1161 |
| SA | Norm | 2.80821 | −4.3006 | 9.91704 | 0.4351 |

TABLE 3

Oneway analysis of CD31shed (% of CD8 cells) by Group

| Level | - Level | Difference | Lower CL | Upper CL | p-Value |
|---|---|---|---|---|---|
| ACS | Carotide | 8.364103 | 2.10954 | 14.61867 | 0.0093* |
| ACS | Norm | 6.664452 | 1.45706 | 11.87185 | 0.0126* |
| ACS | SA | 4.435567 | −0.26376 | 9.13489 | 0.0640 |
| SA | Carotide | 3.928536 | −2.52463 | 10.38171 | 0.2300 |
| SA | Norm | 2.228886 | −3.21545 | 7.67322 | 0.4186 |
| Carotide | Carotide | 1.699650 | −5.13239 | 8.53169 | 0.6227 |

Plasma analysis also confirmed that the level of total soluble CD31 is not able to discriminate between the groups (see Table 4).

TABLE 4

Oneway analysis of total soluble CD31 (ng/ml) by Group

| Level | - Level | Difference | Lower CL | Upper CL | p-Value |
|---|---|---|---|---|---|
| Norm | ACS | 1.017336 | −0.71748 | 2.752148 | 0.2474 |
| Norm | SA | 0.965691 | −0.84806 | 2.779439 | 0.2934 |
| Norm | Carotide | 0.825823 | −1.45023 | 3.101875 | 0.4733 |

TABLE 4-continued

Oneway analysis of total soluble CD31 (ng/ml) by Group

| Level | - Level | Difference | Lower CL | Upper CL | p-Value |
|---|---|---|---|---|---|
| Carotide | ACS | 0.191513 | −1.89216 | 2.275182 | 0.8557 |
| Carotide | SA | 0.139868 | −2.00997 | 2.289702 | 0.8976 |
| SA | ACS | 0.051645 | −1.51391 | 1.617195 | 0.9480 |

Only the method according to the invention, which allows measuring spliced CD31 and shed CD31 in plasma, can be employed for diagnosing and/or prognosing acute coronary syndromes (see Tables 5 and 6, respectively).

TABLE 5

Oneway analysis of spliced CD31 (ng/ml) by Group

| Level | - Level | Difference | Lower CL | Upper CL | p-Value |
|---|---|---|---|---|---|
| Norm | ACS | 4.723988 | 1.97055 | 7.477428 | 0.0010* |
| SA | ACS | 3.288827 | 0.80403 | 5.773619 | 0.0100* |
| Carotide | ACS | 3.255752 | −0.05138 | 6.562888 | 0.0536 |
| Norm | Carotide | 1.468236 | −2.14424 | 5.080714 | 0.4220 |
| Norm | SA | 1.435162 | −1.44356 | 4.313886 | 0.3250 |
| SA | Carotide | 0.033074 | −3.37908 | 3.445224 | 0.9847 |

TABLE 6

Oneway analysis of shed CD31 (ng/ml) by Group

| Level | - Level | Difference | Lower CL | Upper CL | p-Value |
|---|---|---|---|---|---|
| ACS | Norm | 3.707532 | 0.87674 | 6.538321 | 0.0108* |
| ACS | SA | 3.238062 | 0.68347 | 5.792657 | 0.0135* |
| ACS | Carotide | 3.065120 | −0.33492 | 6.465159 | 0.0767* |
| Carotide | Norm | 0.642412 | −3.07155 | 4.356373 | 0.7322 |
| SA | Norm | 0.469470 | −2.49012 | 3.429064 | 0.7537 |
| Carotide | SA | 0.172942 | −3.33506 | 3.680946 | 0.9223 |

In particular, the proportion of shed soluble CD31 (% of total) is very useful for distinguishing between acute coronary syndrome, stable coronary disease and peripheral atherosclerosis (see Table 7).

TABLE 7

Oneway analysis of shed CD31 (% of Total soluble forms of CD31) by Group

| Level | - Level | Difference | Lower CL | Upper CL | p-Value |
|---|---|---|---|---|---|
| ACS | Norm | 22.00424 | 8.4993 | 35.50915 | 0.0017* |
| ACS | Carotide | 18.24801 | 2.0274 | 34.46865 | 0.0278* |
| ACS | SA | 18.06073 | 5.8735 | 30.24799 | 0.0041* |
| SA | Norm | 3.94351 | −10.1759 | 18.06290 | 0.5808 |
| Carotide | Norm | 3.75623 | −13.9620 | 21.47449 | 0.6750 |
| SA | Carotide | 0.18729 | −16.5484 | 16.92299 | 0.9823 |

Importantly, it was also found that the measure in the plasma of patients of spliced and of shed CD31, and not that of total CD31, allows predicting recurrence of Major Adverse Cardiovascular Events (MACE, such as death, fatal and non fatal myocardial infarction).

TABLE 8

| Oneway analysis of: | 1-way Test, ChiSquare Approximation | | |
|---|---|---|---|
| | ChiSquare | DF | Prob > ChiSq |
| Total CD31 (ng/ml) by MACE | 0.1564 | 1 | 0.6925 |
| Spliced CD31 (ng/ml) by MACE | 5.0064 | 1 | 0.0253* |
| Shed CD31 (ng/ml) by MACE | 4.4985 | 1 | 0.0339* |

Example 8

Shed CD31 as a Diagnostic and/or Prognostic Marker of Inflammatory Diseases

It was investigated whether the measure of soluble spliced and shed CD31 using the method of the invention could help evaluating the risk of treatment failure in patients with chronic inflammatory diseases.

Data from 73 patients affected either by rheumatoid arthritis or spondyloarthritis were collected.

It was found that plasma levels of CD31 were associated both with the patient's outcome and with a positive response to biotherapy (see FIG. 6A). This cannot be predicted by the currently used biomarkers (ESR and CRP).

The above patients suffered from very severe inflammation. In such cases, the level of shed CD31 may increase of several folds above the baseline levels (even above 1000 ng/ml), and consequently lead to a significant increase of total soluble CD31. Therefore, not only shed CD31 but also total soluble CD31 can be used as a biomarker for inflammation when the inflammation is very severe.

However, differentiating shed CD31 form total soluble CD31 is required in patients in which the inflammatory state is less obvious.

Example 9

Measure of the Plasma Levels of Soluble GPVI

The method according to the invention was adapted for measuring plasma levels of soluble GPVI. The soluble form of GPVI is cleaved from platelets upon activation and which could evaluate the occurring of thrombus formation in patients at risk.

A reproducible method for measuring shed GPVI in the plasma using (i) an antibody for capture (coupled to the CBA beads); and (ii) a fluorescently labeled natural ligand of GPVI (convulxin) for the detection has been set up. The antibody for capture was either clone No. 3j24.2 or clone No. 9O12.2. These two monoclonal antibodies are described in patent application No. PCT/US2000/018152, published as WO/2001/000810. These antibodies specifically recognize epitopes located on the ectodomain of GPVI.

No current ELISA can achieve the sensitivity and precision of this new method (see FIG. 6B). Standard curves can be obtained both with recombinant GPVI dimers and with recombinant GPVI monomers. This finding is valuable since GPVI dimerizes upon platelet activation, just before being cleaved. After shedding it circulates both as a dimer and as a monomer, and the function and/or diagnostic value might differ depending on the dimerization status.

The method according to the invention thus allows measuring dimers and monomers shed GPVI in the plasma of individuals.

Specifically detecting the shed form of GPVI can be carried out as follows. GPVI spliced form comprises the cytoplasmic tail and can therefore be detected using specific antibodies recognizing the cytoplasmic tail such as those raised against a maltose-binding protein (MBP)-GPVI cytoplasmic tail fusion protein (Suzuki-Inoue et al. J Biol. Chem. 2002 277:21561-6.). On the other hand, the shed form of GPVI comprises the complete ectodomain. Therefore, the method of the invention is performed either using specific antibodies (anti-tail and anti ectodomain) on separate beads for the capture and fluorescently labeled convulxin for the detection, or vice versa (capture by convulxin-coupled beads and detection by differently labeled fluorescent anti-tail and anti-ectodomain antibodies).

The invention claimed is:

1. A method for detecting a shed ectodomain of a CD31 transmembrane protein among soluble forms of said transmembrane protein in a biological sample, wherein said soluble forms include a soluble splice variant of said transmembrane protein and optionally said shed ectodomain, which comprises the steps of:
   a) providing a bead linked to a capture ligand, which capture ligand specifically binds to a region that is present both on said shed ectodomain and on said splice variant;
   b) providing a first discriminating antibody, which first discriminating antibody is a first type of fluorescently-labelled antibody which specifically binds to an epitope located in a region that is present both on said shed ectodomain and on said splice variant;
   c) providing at least one second discriminating antibody, which second discriminating antibody is a second type of fluorescently-labelled antibody which specifically binds to any one of an epitope selected from the group consisting of (i) an epitope located in a region that is present on said shed ectodomain and absent from said splice variant, and (ii) an epitope which is present on said splice variant and absent from said shed ectodomain;
   d) contacting said bead and antibodies with a biological sample likely to contain said soluble forms of said transmembrane protein;
   e) measuring by flow cytometry the fluorescent signal for each fluorescent label; and
   f) comparing the signal obtained for each fluorescent label, wherein a difference in the signals measured at step (e) indicates that the biological sample comprises said shed ectodomain.

2. The method according to claim 1, wherein:
   i) said soluble forms include at least three soluble forms;
   ii) the discriminating antibodies are chosen in such a way as to discriminate between said soluble forms; and
   iii) the capture ligand specifically binds to a region that is present on all said soluble forms.

3. The method according to claim 1, wherein said capture ligand is an antibody.

4. The method according to claim 1, further comprising the step of calculating the percentage and/or the amount of said soluble forms that corresponds to said shed ectodomain.

5. The method according to claim 1, further comprising the step of calculating either the ratio of shed ectodomain to soluble forms, or the ratio of soluble splice variant to soluble forms.

6. The method according to claim 1, wherein the first discriminating antibody specifically binds to an epitope located in the first extracellular immunoglobulin-like domain of CD31, and wherein the second discriminating antibody specifically binds to an epitope located in the sixth extracellular immunoglobulin-like domain of CD31.

7. The method according to claim 1, wherein:
   a. the first discriminating antibody specifically binds to an epitope located in the first extracellular immunoglobulin-like domain of CD31;
   b. the second discriminating antibody specifically binds to an epitope located in the sixth extracellular immunoglobulin-like domain of CD31; and
   c. the discriminating antibodies further comprise an antibody which specifically binds to an epitope located in the fifth extracellular immunoglobulin-like domain of CD31.

8. The method according to claim 1, wherein said biological sample is plasma obtained from an individual suffering from or at risk of suffering from a thrombotic or an autoimmune disorder.

9. A diagnostic kit comprising:
   i) a bead linked to an antibody that specifically binds to an epitope located in a region that is present both on a shed ectodomain of a CD31 transmembrane protein and on a soluble splice variant of said transmembrane protein;
   ii) a first type of fluorescently-labelled antibody that specifically binds to any one of an epitope selected from the group consisting of (i) an epitope located in a region that is present on said shed ectodomain and absent from said soluble splice variant, and (ii) an epitope which is present on said soluble splice variant and absent from said shed ectodomain; and
   iii) a second type of fluorescently-labelled antibody that specifically binds to an epitope located in a region that is present both on said shed ectodomain and on said soluble splice variant.

* * * * *

SEQUENCE LISTING

```
<160> NUMBER OF SEQ ID NOS: 4

<210> SEQ ID NO 1
<211> LENGTH: 738
<212> TYPE: PRT
<213> ORGANISM: Homo sapiens
<220> FEATURE:
<221> NAME/KEY: SIGNAL
<222> LOCATION: (1)..(27)
<220> FEATURE:
<221> NAME/KEY: DOMAIN
<222> LOCATION: (28)..(601)
<223> OTHER INFORMATION: extracellular domain
<220> FEATURE:
<221> NAME/KEY: DOMAIN
<222> LOCATION: (34)..(121)
<223> OTHER INFORMATION: First Ig-like domain
<220> FEATURE:
<221> NAME/KEY: DOMAIN
<222> LOCATION: (145)..(233)
<223> OTHER INFORMATION: Second Ig-like domain
<220> FEATURE:
<221> NAME/KEY: DOMAIN
<222> LOCATION: (236)..(315)
<223> OTHER INFORMATION: Third Ig-like domain
<220> FEATURE:
<221> NAME/KEY: DOMAIN
<222> LOCATION: (328)..(401)
<223> OTHER INFORMATION: Fourth Ig-like domain
<220> FEATURE:
<221> NAME/KEY: DOMAIN
<222> LOCATION: (424)..(493)
<223> OTHER INFORMATION: Fifth Ig-like domain
<220> FEATURE:
<221> NAME/KEY: DOMAIN
<222> LOCATION: (499)..(591)
<223> OTHER INFORMATION: Sixth Ig-like domain
<220> FEATURE:
<221> NAME/KEY: DOMAIN
<222> LOCATION: (592)..(601)
<223> OTHER INFORMATION: Juxta-membrane domain
<220> FEATURE:
<221> NAME/KEY: DOMAIN
<222> LOCATION: (602)..(620)
<223> OTHER INFORMATION: transmembrane domain
<220> FEATURE:
<221> NAME/KEY: DOMAIN
<222> LOCATION: (621)..(738)
<223> OTHER INFORMATION: cytoplasmic

<400> SEQUENCE: 1

Met Gln Pro Arg Trp Ala Gln Gly Ala Thr Met Trp Leu Gly Val Leu
 1               5                  10                  15

Leu Thr Leu Leu Leu Cys Ser Ser Leu Glu Gly Gln Glu Asn Ser Phe
                20                  25                  30

Thr Ile Asn Ser Val Asp Met Lys Ser Leu Pro Asp Trp Thr Val Gln
            35                  40                  45

Asn Gly Lys Asn Leu Thr Leu Gln Cys Phe Ala Asp Val Ser Thr Thr
        50                  55                  60

Ser His Val Lys Pro Gln His Gln Met Leu Phe Tyr Lys Asp Asp Val
65                  70                  75                  80

Leu Phe Tyr Asn Ile Ser Ser Met Lys Ser Thr Glu Ser Tyr Phe Ile
                85                  90                  95
```

-continued

```
Pro Glu Val Arg Ile Tyr Asp Ser Gly Thr Tyr Lys Cys Thr Val Ile
            100                 105                 110

Val Asn Asn Lys Glu Lys Thr Thr Ala Glu Tyr Gln Leu Leu Val Glu
        115                 120                 125

Gly Val Pro Ser Pro Arg Val Thr Leu Asp Lys Lys Glu Ala Ile Gln
    130                 135                 140

Gly Gly Ile Val Arg Val Asn Cys Ser Val Pro Glu Glu Lys Ala Pro
145                 150                 155                 160

Ile His Phe Thr Ile Glu Lys Leu Glu Leu Asn Glu Lys Met Val Lys
                165                 170                 175

Leu Lys Arg Glu Lys Asn Ser Arg Asp Gln Asn Phe Val Ile Leu Glu
            180                 185                 190

Phe Pro Val Glu Glu Gln Asp Arg Val Leu Ser Phe Arg Cys Gln Ala
        195                 200                 205

Arg Ile Ile Ser Gly Ile His Met Gln Thr Ser Glu Ser Thr Lys Ser
    210                 215                 220

Glu Leu Val Thr Val Thr Glu Ser Phe Ser Thr Pro Lys Phe His Ile
225                 230                 235                 240

Ser Pro Thr Gly Met Ile Met Glu Gly Ala Gln Leu His Ile Lys Cys
                245                 250                 255

Thr Ile Gln Val Thr His Leu Ala Gln Glu Phe Pro Glu Ile Ile Ile
            260                 265                 270

Gln Lys Asp Lys Ala Ile Val Ala His Asn Arg His Gly Asn Lys Ala
        275                 280                 285

Val Tyr Ser Val Met Ala Met Val Glu His Ser Gly Asn Tyr Thr Cys
    290                 295                 300

Lys Val Glu Ser Ser Arg Ile Ser Lys Val Ser Ser Ile Val Val Asn
305                 310                 315                 320

Ile Thr Glu Leu Phe Ser Lys Pro Glu Leu Glu Ser Ser Phe Thr His
                325                 330                 335

Leu Asp Gln Gly Glu Arg Leu Asn Leu Ser Cys Ser Ile Pro Gly Ala
            340                 345                 350

Pro Pro Ala Asn Phe Thr Ile Gln Lys Glu Asp Thr Ile Val Ser Gln
        355                 360                 365

Thr Gln Asp Phe Thr Lys Ile Ala Ser Lys Ser Asp Ser Gly Thr Tyr
    370                 375                 380

Ile Cys Thr Ala Gly Ile Asp Lys Val Val Lys Lys Ser Asn Thr Val
385                 390                 395                 400

Gln Ile Val Val Cys Glu Met Leu Ser Gln Pro Arg Ile Ser Tyr Asp
                405                 410                 415

Ala Gln Phe Glu Val Ile Lys Gly Gln Thr Ile Glu Val Arg Cys Glu
            420                 425                 430

Ser Ile Ser Gly Thr Leu Pro Ile Ser Tyr Gln Leu Leu Lys Thr Ser
        435                 440                 445

Lys Val Leu Glu Asn Ser Thr Lys Asn Ser Asn Asp Pro Ala Val Phe
    450                 455                 460

Lys Asp Asn Pro Thr Glu Asp Val Glu Tyr Gln Cys Val Ala Asp Asn
465                 470                 475                 480

Cys His Ser His Ala Lys Met Leu Ser Glu Val Leu Arg Val Lys Val
                485                 490                 495

Ile Ala Pro Val Asp Glu Val Gln Ile Ser Ile Leu Ser Ser Lys Val
            500                 505                 510
```

```
Val Glu Ser Gly Glu Asp Ile Val Leu Gln Cys Ala Val Asn Glu Gly
            515                 520                 525

Ser Gly Pro Ile Thr Tyr Lys Phe Tyr Arg Glu Lys Glu Gly Lys Pro
    530                 535                 540

Phe Tyr Gln Met Thr Ser Asn Ala Thr Gln Ala Phe Trp Thr Lys Gln
545                 550                 555                 560

Lys Ala Ser Lys Glu Gln Gly Glu Tyr Tyr Cys Thr Ala Phe Asn
                565                 570                 575

Arg Ala Asn His Ala Ser Ser Val Pro Arg Ser Lys Ile Leu Thr Val
                580                 585                 590

Arg Val Ile Leu Ala Pro Trp Lys Lys Gly Leu Ile Ala Val Val Ile
            595                 600                 605

Ile Gly Val Ile Ile Ala Leu Leu Ile Ile Ala Lys Cys Tyr Phe
    610                 615                 620

Leu Arg Lys Ala Lys Ala Lys Gln Met Pro Val Glu Met Ser Arg Pro
625                 630                 635                 640

Ala Val Pro Leu Leu Asn Ser Asn Asn Glu Lys Met Ser Asp Pro Asn
                645                 650                 655

Met Glu Ala Asn Ser His Tyr Gly His Asn Asp Asp Val Arg Asn His
                660                 665                 670

Ala Met Lys Pro Ile Asn Asp Asn Lys Glu Pro Leu Asn Ser Asp Val
            675                 680                 685

Gln Tyr Thr Glu Val Gln Val Ser Ser Ala Glu Ser His Lys Asp Leu
    690                 695                 700

Gly Lys Lys Asp Thr Glu Thr Val Tyr Ser Glu Val Arg Lys Ala Val
705                 710                 715                 720

Pro Asp Ala Val Glu Ser Arg Tyr Ser Arg Thr Glu Gly Ser Leu Asp
                725                 730                 735

Gly Thr

<210> SEQ ID NO 2
<211> LENGTH: 23
<212> TYPE: PRT
<213> ORGANISM: Artificial
<220> FEATURE:
<223> OTHER INFORMATION: human-derived CD31 peptide

<400> SEQUENCE: 2

Asn His Ala Ser Ser Val Pro Arg Ser Lys Ile Leu Thr Val Arg Val
1               5                   10                  15

Ile Leu Ala Pro Trp Lys Lys
            20

<210> SEQ ID NO 3
<211> LENGTH: 23
<212> TYPE: PRT
<213> ORGANISM: Artificial
<220> FEATURE:
<223> OTHER INFORMATION: mouse-derived CD31 peptide

<400> SEQUENCE: 3

Ser Ser Met Arg Thr Ser Pro Arg Ser Ser Thr Leu Ala Val Arg Val
1               5                   10                  15

Phe Leu Ala Pro Trp Lys Lys
            20

<210> SEQ ID NO 4
<211> LENGTH: 23
```

```
<212> TYPE: PRT
<213> ORGANISM: Artificial
<220> FEATURE:
<223> OTHER INFORMATION: scramble peptide

<400> SEQUENCE: 4

Ser Met Pro Ala Val Arg Ser Arg Phe Ser Ala Thr Ser Leu Val Thr
1               5                   10                  15

Leu Lys Ser Arg Trp Pro Lys
            20
```